(12) United States Patent
Michel et al.

(10) Patent No.: US 9,387,212 B2
(45) Date of Patent: Jul. 12, 2016

(54) METHODS FOR TREATING PARKINSON'S DISEASE

(71) Applicant: UCB Pharma S.A., Brussels (BE)

(72) Inventors: Anne Michel, Brussels (BE); Patrick Downey, Brussels (BE); Florian Montel, Brussels (BE); Dieter Scheller, Brussels (BE); Bernard Christophe, Brussels (BE)

(73) Assignee: UCB Biopharma SPRL, Brussels (BE)

( * ) Notice: Subject to any disclaimer, the term of this patent is extended or adjusted under 35 U.S.C. 154(b) by 0 days.

(21) Appl. No.: 14/395,533

(22) PCT Filed: Apr. 19, 2013

(86) PCT No.: PCT/EP2013/058212
§ 371 (c)(1),
(2) Date: Oct. 20, 2014

(87) PCT Pub. No.: WO2013/156614
PCT Pub. Date: Oct. 24, 2013

(65) Prior Publication Data
US 2015/0157638 A1 Jun. 11, 2015

Related U.S. Application Data

(60) Provisional application No. 61/636,054, filed on Apr. 20, 2012.

(51) Int. Cl.
| | | |
|---|---|---|
| *A61K 31/5377* | (2006.01) | |
| *A61K 31/195* | (2006.01) | |
| *A61K 31/198* | (2006.01) | |
| *A61K 31/445* | (2006.01) | |
| *A61K 31/451* | (2006.01) | |
| *A61K 31/495* | (2006.01) | |
| *A61K 31/497* | (2006.01) | |
| *A61K 31/501* | (2006.01) | |
| *A61K 31/506* | (2006.01) | |
| *A61K 31/519* | (2006.01) | |
| *A61K 31/52* | (2006.01) | |
| *A61K 31/423* | (2006.01) | |
| *A61K 31/5415* | (2006.01) | |
| *A61K 45/06* | (2006.01) | |
| *A61K 31/454* | (2006.01) | |

(52) U.S. Cl.
CPC ........... *A61K 31/5377* (2013.01); *A61K 31/195* (2013.01); *A61K 31/198* (2013.01); *A61K 31/423* (2013.01); *A61K 31/445* (2013.01); *A61K 31/451* (2013.01); *A61K 31/454* (2013.01); *A61K 31/495* (2013.01); *A61K 31/497* (2013.01); *A61K 31/501* (2013.01); *A61K 31/506* (2013.01); *A61K 31/519* (2013.01); *A61K 31/52* (2013.01); *A61K 31/5415* (2013.01); *A61K 45/06* (2013.01)

(58) Field of Classification Search
CPC ............... C07D 413/14; C07D 417/14; A61K 31/5377; A61K 31/195; A61K 31/198; A61K 31/445; A61K 31/451; A61K 31/454; A61K 31/495; A61K 31/497; A61K 31/501; A61K 31/506; A61K 31/519; A61K 31/52; A61K 45/06
See application file for complete search history.

(56) References Cited

FOREIGN PATENT DOCUMENTS

| CH | WO 2005116026 A1 * 12/2005 | ............ C07D 417/12 |
|---|---|---|
| WO | WO 2010022304 A1 * 2/2010 | ............ A61K 31/13 |
| WO | 2012/038980 A2 3/2012 | |

OTHER PUBLICATIONS

Lara et al., "Chronic treatment with caffeine blunts the hyperlocomotor but not cognitive effects of the NMDA receptor antagonist MK-801 in mice", Schizophrenia Research, 2003, 60(1), 110-111.
Hallett et al., "Rationale for and use of NMDA receptor antagonists in Parkinson's disease", Pharmacology & Therapeutics, 2004, 102(2), 155-174.
Warraich et al., "Evaluation of behavioural effects of a selective NMDA NR1A/2B receptor antagonist in the unilateral 6-OHDA lesion rat model", Brain Research Bulletin, 2009, 78(2-3), 85-90.
Xu et al., "Therapeutic potential of adenosine A2A receptor antagonists in Parkinson's disease", Pharmacology and Therapeutics, 2005, 105(3), 267-310.
Rose et al., "The novel adenosine A2a receptor antagonist ST1535 potentiates the effects of a threshold dose of L-DOPA in MPTP treated common marmosets", European Journal of Pharmacology, 2006, 546(1-3), 82-87.
Agnati et al., "Neuroprotective effect of L-DOPA co-administered with the adenosine A2A receptor agonist CGS 21680 in an animal model of Parkinson's disease", Brain Research Bulletin, 2004, 64(2), 155-164.
Aguiar et al., "Neuroprotective effects of caffeine in the model of 6-hydroxydopamine lesion in rats", Pharmacology Biochemistry and Behavior, 2006, 84(3), 415-419.

* cited by examiner

*Primary Examiner* — Sarah Pihonak
(74) *Attorney, Agent, or Firm* — McDonnell Boehnen Hulbert & Berghoff LLP

(57) ABSTRACT

The invention pertains to a method of treating Parkinson's disease (PD) in a mammal, comprising administering a first pharmaceutical agent and a second pharmaceutical agent, wherein the first pharmaceutical agent is an antagonist of the adenosine receptor 2 ($A_{2A}$) and the second pharmaceutical agent is an antagonist of the N-methyl-D-aspartate (NMDA) receptor subtype NR2B.

12 Claims, 13 Drawing Sheets

Figure 2:
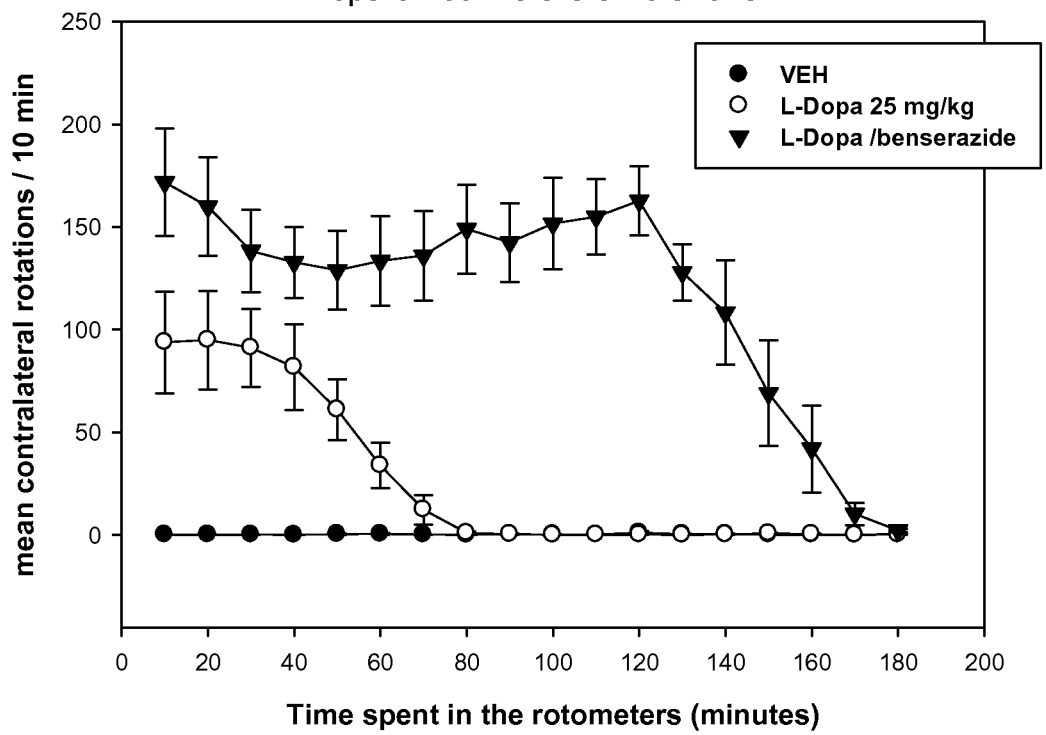

Figure 1
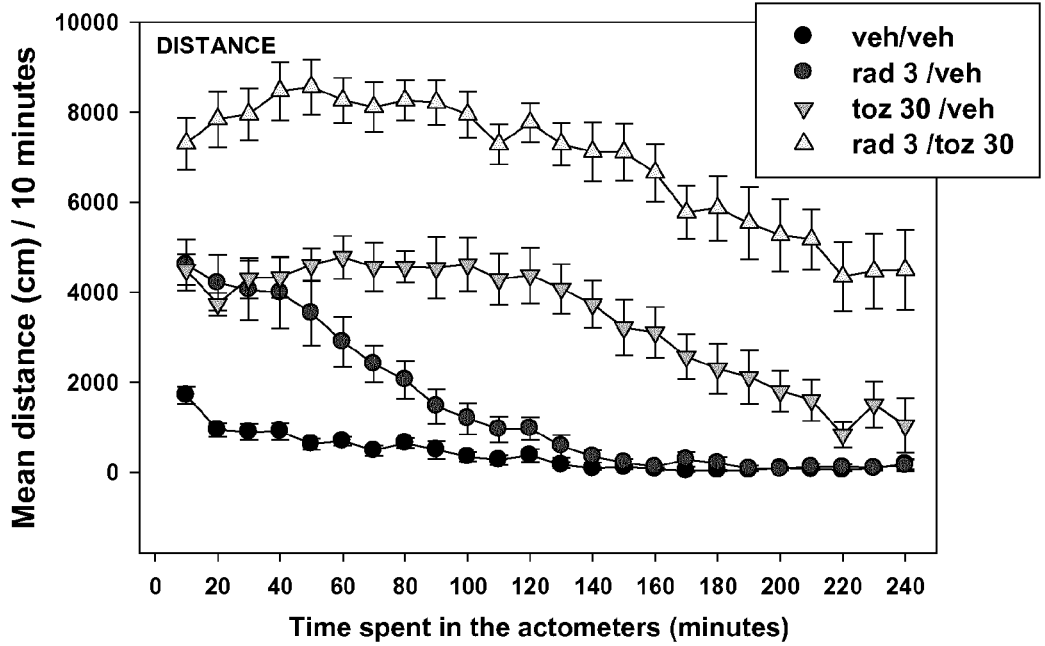
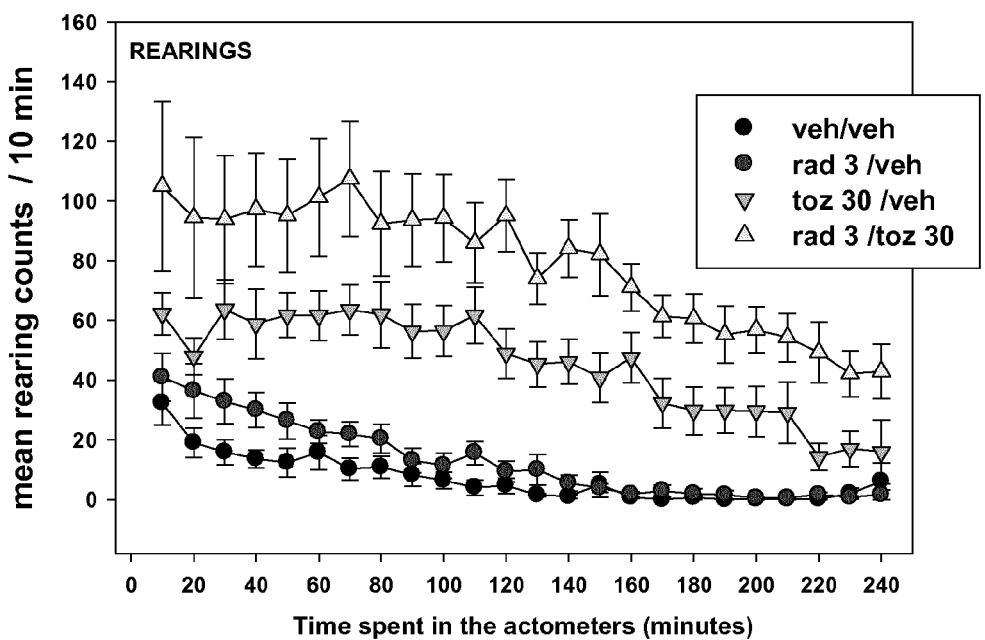

Figure 3
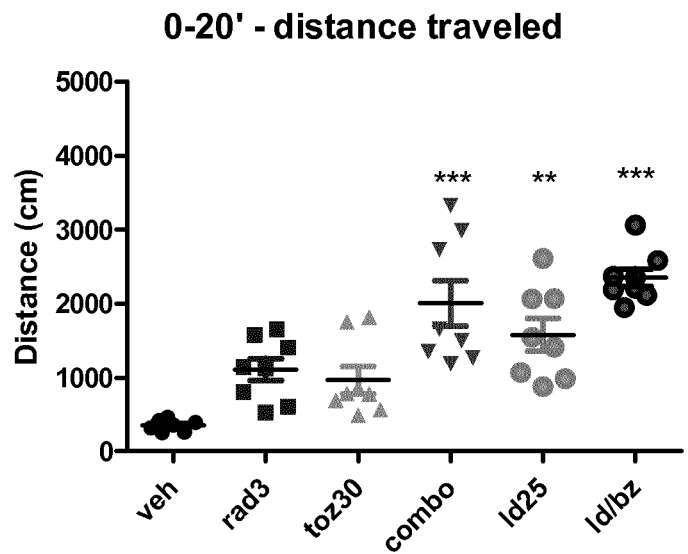
, p<0.01, *p<0.001: significantly different from the vehicle-treated group
(Dunn's Multiple Comparison test)
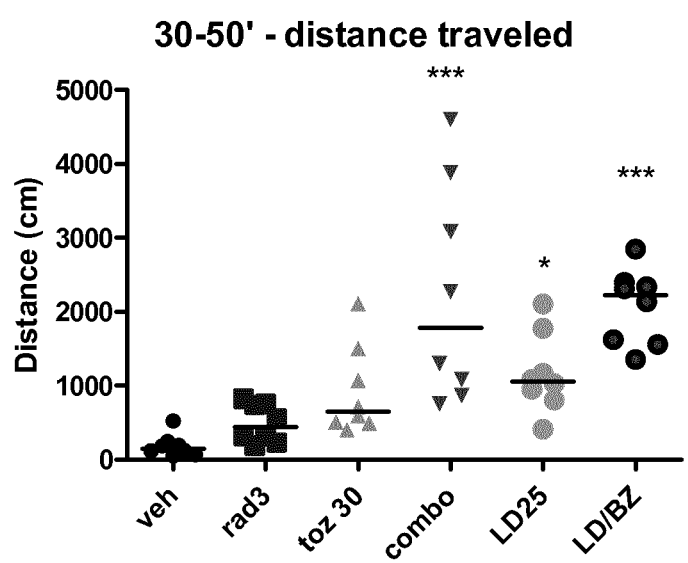
*, p<0.05, ***p<0.001: significantly different from the VEH-treated
group (Dunn's Multiple Comparison test)

Figure 4

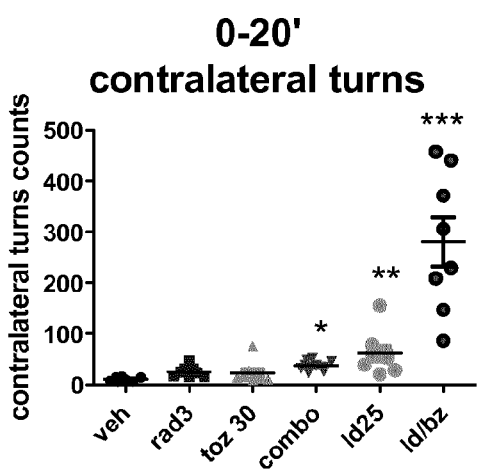

*, p<0.05, , p<0.01, *p<0.001:
significantly different from the
VEH-treated group
(Dunn's Multiple Comparison test)

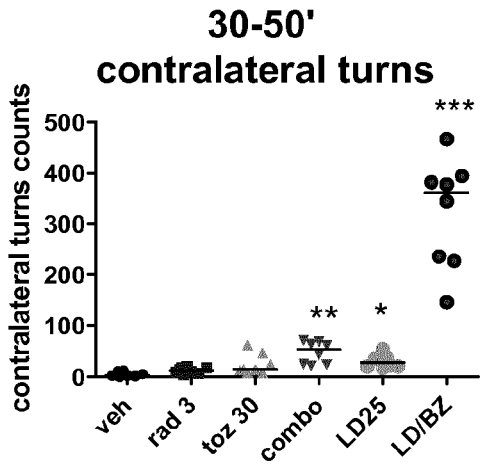

*, p<0.05, , p<0.01, *, p<0.001:
significantly different from the
VEH-treated group (Dunn's Multiple
Comparison test)

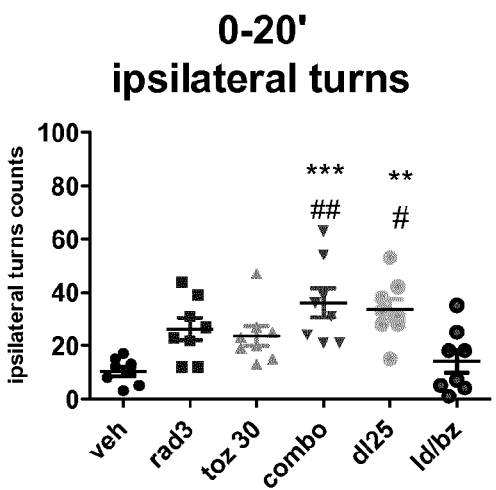

, p<0.01, *p<0.001: significantly
different from the vehicle-treated group. #,
p<0.05, ##, p<0.01: mean significantly
different from that of the LD/BZ-treated
group (Tukey post hoc test)

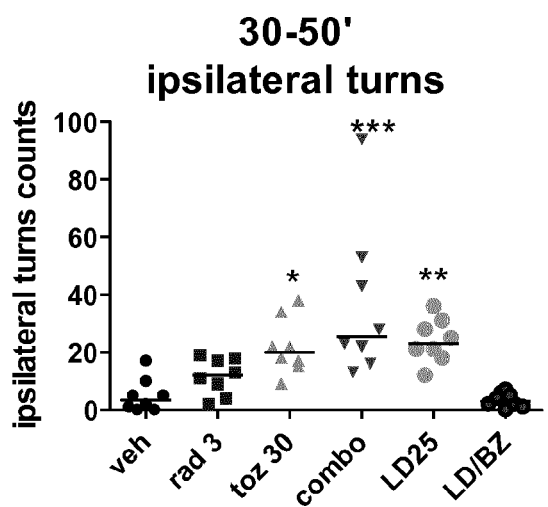

*, p<0.05, , p<0.01, *, p<0.001:
significantly different from the
VEH-treated group (Dunn's Multiple
Comparison test)

Figure 5

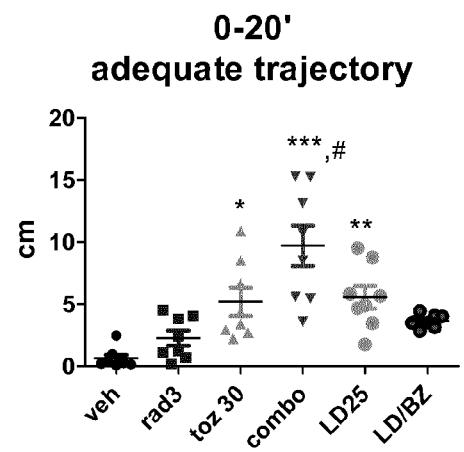

0-20'
adequate trajectory

*, p<0.05, p<0.01,*,p<0.001: significantly
different from the VEH-treated group
(Dunn's Multiple Comparison test) #, p<0.05:
mean significantly different from the rad
3-treated group.

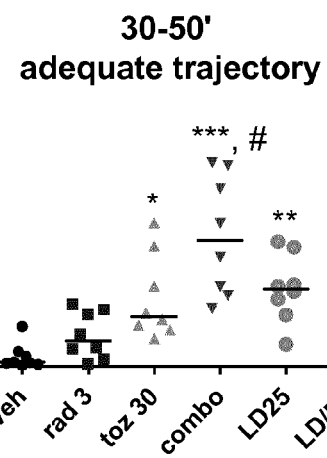

30-50'
adequate trajectory

*, p<0.05,, p<0.01, *, p<0.001: significantly
different from the VEH-treated group (Dunn's
Multiple Comparison test)
, p<0.05: significantly different form the
rad3-treated group.

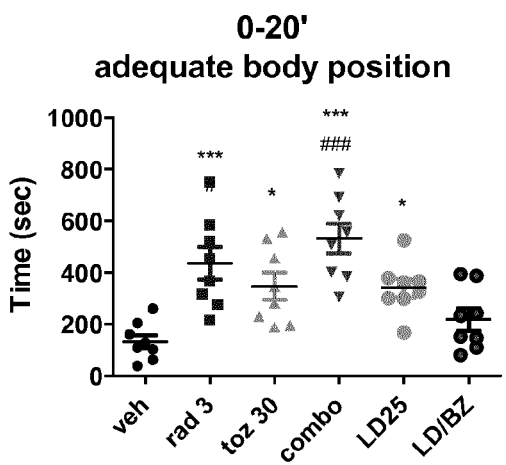

0-20'
adequate body position

*, p<0.05, ***p<0.001: significantly different
from the vehicle-treated group; #, p<0.05, ###,
p<0.001: significantly different from the LD/BZ
(Tukey post hoc test)

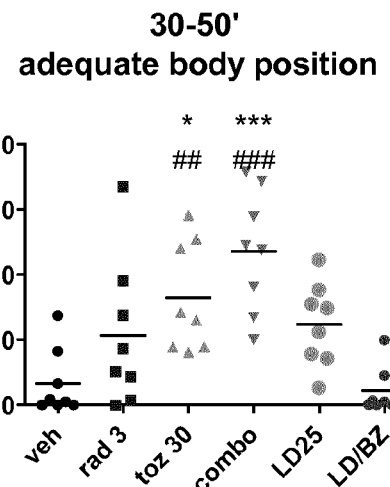

30-50'
adequate body position

*, p<0.05; ***, p<0.001: significantly different from
the veh-treated groups. #, p<0.05; ##, p<0.01:
significantly different from the LD/BZ-treated
group (Tukey post hoc test).

*, p<0.05;, p<0.01; *, p<0.001: significantly different from the vehicle group (Dunn's Multiple Comparison test)

*, p<0.05; ***, p<0.001: significantly different from the vehicle group (Dunn's Multiple Comparison test)

*, p<0.05; ***, p<0.001: significantly different from the vehicle group
(Dunn's Multiple Comparison test)

*, p<0.05: significantly different from the vehicle group (Dunn's Multiple Comparison test)

*, p<0.05; ***, p<0.001: significantly different from the vehicle group (Dunn's Multiple comparison test)

Data represent mean +/- sem of 8 Sprague-Dawley rats per group.
Vehicle, Radiprodil or/and Tozadenant were orally administered 15
minutes before L-Dopa administrations. (25mg/kg; ip).
Rats were habituated 10 minutes into testing arena before starting
data recording;

, p<0.05: mean significantly different from that of all of the
three other groups (LSD post hoc test)

Figure 14:

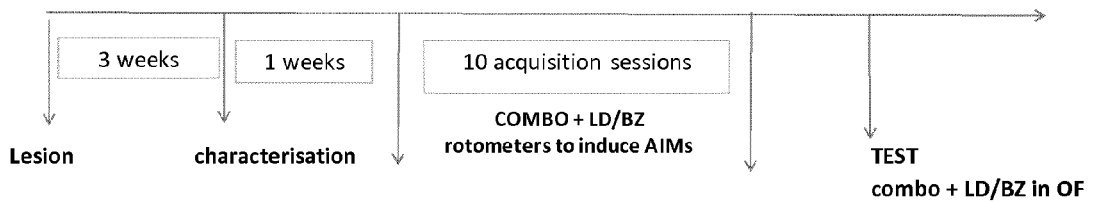

Week 1    surgery

Week 3    characterization with apomorphine 0.05 mg/kg (sc)
week 4-5  chronic treatment with combo + LD 14/BZ3.5 (oid)
          placement in small rotometers
          rotations record: every day
          video record: A1 - A5 - A10
          objective: induce the development of AIMs week 6    4 groups: treat 1 + treat 2 + LD/BZ but placement in open-field for automated behavioral scoring
          objective: assess the behavioral profile in larger environment

*, p<0.05: mean significantly different from that of the first acquisition session for each respective treatment (planne contrasts).
, p<0.001: the combo-treated group is significantly more active than the other three groups (Tukey post hoc test).

METHODS FOR TREATING PARKINSON'S DISEASE

This application is a U.S. national phase of International Application No. PCT/EP2013/058212 filed on Apr. 19, 2013, which claims priority to U.S. Provisional Application No. 61/636,054 filed on Apr. 20, 2012.

FIELD OF THE INVENTION

The invention relates to compositions and methods for treating Parkinson's disease or to counteract the symptoms of Parkinson's disease.

BACKGROUND OF THE INVENTION

Parkinson's disease (PD) is a degenerative disorder of the central nervous system. The motor symptoms of Parkinson's disease result from the death of dopamine-generating cells in the substantia nigra, a region of the midbrain; the cause of this cell death is unknown. By the time clinical symptoms of PD become evident, approximately 70-80% of striatal dopaminergic neurons have been lost. Early in the course of the disease, the most obvious symptoms are movement-related. Later, cognitive and behavioural problems may arise, with dementia commonly occurring in the advanced stages of the disease. However, while dopaminergic treatment is able to effectively treat the motor symptoms at the early stages of the disease, it is not a satisfactory treatment as its efficacy wears off in the later stages of disease and its prolonged use leads to motor complications.

The cardinal motor symptoms of Parkinson's disease (PD), bradykinesia, akinesia and resting tremor result from a decrease in striatal DA content which causes an imbalance in the neuronal circuits.

DA (Dopamine) replacement therapies using the DA precursor L-dihydroxyphenylalanine (L-Dopa) or dopamine (D)2/3 receptor agonists are the mainstay of current treatment strategies. However, such treatments manage the primary disease clinical symptoms only and do nothing to treat the underlying causes of the disease, i.e. the progressive loss of dopaminergic cells. Instead, they can complicate the situation due to the induction of abnormal involuntary movements (AIMs) or dyskinesia. Furthermore, the long-term treatment with L-Dopa is accompanied by unpredictable fluctuations of its effects. Novel strategies are therefore needed to treat the motor symptoms, to ameliorate or prevent dyskinesia and also to delay, prevent or reverse dopaminergic neuronal loss. Thus, therapeutic agents interfering with one or ideally with several of these events could potentially lead to a novel class of drugs perhaps with disease modifying properties for PD.

These novel drugs are expected to be as efficacious as L-Dopa but should not induce motor fluctuations or cross-sensitize with dopaminergic treatment.

In the early stages of PD, L-Dopa is metabolised to dopamine which is stored in surviving presynaptic dopaminergic terminals in the striatum (serving as storage and buffer). Its release is controlled if feed-back loops are intact. However, as more and more terminals are lost, the storage and buffering capacity for dopamine is lost and the duration of L-Dopa's effect shortens. Thus, the oral intake and subsequent pulsatile exposure of the basal ganglia provokes peak-dose dyskinesia and or motor fluctuations. Once the nigral degeneration has developed to a level that motor symptoms occur, a single injection of L-Dopa is sufficient to establish a response which is called 'priming' (Morelli et al., 1987; Delfino et al., 2004): Once L-Dopa has been administered and induced dyskinesia, each subsequent drug exposure will provoke that response—even if it had not been administered for several weeks. The weak NMDA (N-methyl-d-aspartate) receptor antagonist amantadine can reduce dyskinesia intensity, suggesting that over-activity of glutamatergic inputs in the basal ganglia is involved in priming and dyskinesia (Blanchet et al., 1998). Clinical and preclinical studies provide evidence of altered glutamatergic function in the striatum in dyskinetic animals and patients, including changes in expression, phosphorylation and synaptic organization of glutamate receptors (Chase et al., 2000). Furthermore, NMDA receptors containing NR2B subunits are enriched in the striatum and there is evidence that AMPA (a-amino-3-hydroxy-5-methyl-4-isoxazole propionic acid) receptor antagonists can also suppress dyskinesia (Bibbiani et al., 2005). These data seem to indicate that dyskinesia involves an abnormal glutamatergic corticostriatal input.

In order to reverse established dyskinesia or to prevent dyskinesia from occurring in the first place, one approach would be to replace dopaminergic treatment early on in the therapy. Due to their unique distribution within the basal ganglia and their interactions with dopamine-related intracellular signalling cascades, $A_{2A}$ antagonists and NR2B-subunit selective NMDA antagonists have been developed. However, clinical trials with $A_{2A}$ antagonists (Istradefylline, Mizuno et al. 2010) or NR2B antagonist (Traxoprodil, Nutt et al., 2008) as treatments in PD patients did not show the expected efficacy.

As already mentioned, priming is classically defined as the process by which the brain becomes sensitized such that administration of a dopaminergic therapy modifies the response to subsequent dopaminergic treatment. Priming is induced by acute dopamimetic treatment in a denervated brain.

The unilateral 6-hydroxydopamine (6-OHDA)-lesioned rat model may represent a quantitative model of priming. Such 6-OHDA-lesioned rats chronically treated with dopaminergic drugs (L-Dopa or dopamine agonists) develop a progressive increase of contralateral rotations (i.e. away from the side of the lesion), which is called "behavioural sensitization". In this model, administration of a so-called 'priming" dose of DA receptor agonist sensitizes the animal to the effect of a subsequent challenge with DA agonists.

A phenomenon of "cross-sensitization" may be observed when a subject becomes sensitized to substance different from the substance to which the subjects is already sensitized.

Cross-sensitization has already been observed between caffeine- and l-dopa-induced behaviours in hemiparkinsonian mice (Yu et al., 2006).

Adenosine receptors represent a subclass of the group of purine nucleotide and nucleoside G protein-coupled receptors known as purinoceptors; the main pharmacologically distinct adenosine receptor subtypes are known as $A_1$, $A_{2A}$, $A_{2B}$, and $A_3$. The dominant adenosine receptor subtypes in the brain are $A_1$ and $A_{2A}$. While the $A_1$ adenosine receptor subtype is found throughout the brain at high density, the distribution of the $A_{2A}$ receptor is more restricted; it is found at high density in the striatum (caudate-putamen, nucleus accumbens, olfactory tubercule), where it is co-localized with the dopamine D2 receptor on striatopallidal output neurons. The discrete localization of the $A_{2A}$ receptor within the striatum and its ability to functionally antagonize the actions of the D2 receptor has led to the suggestion of the potential utility of $A_{2A}$ receptor antagonists for the symptomatic treatment of Parkinson's disease (PD).

N-methyl-D-aspartate (NMDA) receptors are heteromeric assemblies of subunits. Two principal subunit families are designated NR1 and NR2. The NR2 subunit family is divided into four subunit types which are: NR2A, NR2B, NR2C, NR2D which display different physiological and pharmacological properties such as ion gating, magnesium sensitivity, pharmacological profile, and in anatomical distribution.

While NMDA receptor inhibition has therapeutic utility primarily in the treatment of pain and neurodegenerative diseases, there are significant liabilities to many available NMDA receptor antagonists that can cause potentially serious side effects. The more discrete distribution of the NR2B subunit in the central nervous system may support a reduced side-effect profile of agents that act selectively at this site. However, even selective NR2B antagonists may exhibit low affinity towards the NR2B subunit of the NMDA receptor. Also, some NR2B antagonists which are said to be NR2B selective might not be entirely specific.

Hauber and Munkle (1996) alleged that the anti-cataleptic effects of the NMDA receptor antagonists CGP37849 (competitive) and dizocilpine (MK-801, non-competitive) may be potentiated by co-administration of the non-selective adenosine receptor antagonist/phospho-diesterase inhibitor theophylline.

SUMMARY OF THE INVENTION

The invention relates to compositions and methods for treating Parkinson's disease or to counteract the symptoms of or associated with Parkinson's disease or to counteract the side-effects of the treatment of Parkinson's disease.

The first aspect of the present invention pertains to a method of treating Parkinson's disease (PD) in a mammal, comprising administering a first pharmaceutical agent and a second pharmaceutical agent, wherein the first pharmaceutical agent is an antagonist of the adenosine receptor 2 ($A_{2A}$) and the second pharmaceutical agent is an antagonist of the N-methyl-D-aspartate (NMDA) receptor subtype NR2B.

A second aspect of the present invention pertains to a method of treating Parkinson's disease whereby the $A_{2A}$ antagonist and the NR2B antagonist are essentially administered together with L-Dopa. The $A_{2A}$ antagonist and the NR2B antagonist are either administered in the early phase of the diseases and prior to the use of L-Dopa or in conjunction with L-Dopa once its administration has been initiated.

A third aspect of the present invention pertains to a pharmaceutical composition comprising a therapeutically effective amount of a combination of an adenosine $A_{2A}$ receptor antagonist and a NR2B antagonist in a pharmaceutical acceptable carrier or excipients.

A fourth aspect of the present invention pertains to a kit of parts comprising:
(a) a first containment containing a pharmaceutical formulation comprising a therapeutically effective amount of an $A_{2A}$ receptor antagonist and
(b) a second containment containing a pharmaceutical formulation comprising a therapeutically effective amount of the NR2B antagonist.

Further aspects of the invention will become apparent from the detailed specification.

DETAILED DESCRIPTION OF THE INVENTION

The main aspect of this invention consists in a method of treating Parkinson's disease (PD) in a mammal, comprising administering a first pharmaceutical agent and a second pharmaceutical agent, wherein the first pharmaceutical agent is an antagonist of the adenosine receptor 2 ($A_{2A}$) and the second pharmaceutical agent is an antagonist of the N-methyl-D-aspartate (NMDA) receptor subtype NR2B.

An $A_{2A}$ antagonist is a chemical compound or a peptide or a protein that blocks or counteracts the function of the $A_{2A}$ receptor, either by orthosteric interaction or by allosteric interaction. That is, an agent which will prevent the endogenous ligand adenosine or an $A_{2A}$ agonist from stimulating the receptor and eliciting an effect. Importantly, the present invention is based on the use of an $A_{2A}$ antagonist, i.e. a selective adenosine receptor antagonist.

An NR2B antagonist is a chemical compound or a peptide or a protein that blocks or counteracts the function of the NR2B receptor, all NR2B selective antagonists identified thus far act by binding to an allosteric site on the receptor. Activation of the NR2B receptor by the co-agonists glutamate and glycine (or NMDA) leads to the influx of calcium which can be prevented by an antagonist.

A great variety of $A_{2A}$ antagonists is known and has been claimed, e.g. in the following international patent applications, the disclosure of which is herein incorporated by reference: WO 2012/03898, WO 2011/06152, WO 2011/06020, WO 2011/053507, WO 2010/040003, WO 2010/037122, WO 2009/055308, WO 2009/050198, WO 2008/055711, WO 2007/047293, WO 2007/038212, WO 2006/137527, WO 2006/129626, WO 2006/124770, WO 2006/083949, WO 2012/03898, WO 2011/06152, WO 2011/06020, WO 2011/05350, WO 2010/04000, WO 2010/03712, WO 2009/055308, WO 2009/050198, WO 2008/055711, WO 2007/047293, WO 2007/038212, WO 2006/137527, WO 2006/129626, WO 2006/124770, WO 2006/083949.

Known $A_{2A}$ antagonists include the following, whereby some are in clinical development:
Istradefylline (KW-6002)
MSX-3
Preladenant (SCH-420,814)
PFB-509
SCH-58261
SCH-412,348
SCH-442,416
SCH-800900
ST-1535
ST-4206
Caffeine
VER-6623
VER-6947
VER-7835
V-81444
Vipadenant (BIIB-014)
ZM-241,385

A preferred $A_{2A}$ antagonist is selected from the group comprising Istradefylline (KW-6002), ASP5854, Vipadenant (BIIB014), ST-1535, Preladenant (SCH420814), SYN-115, ZM-241,385, V-81444.

The chemical structure of istradefylline (KW-6002) is as follows:

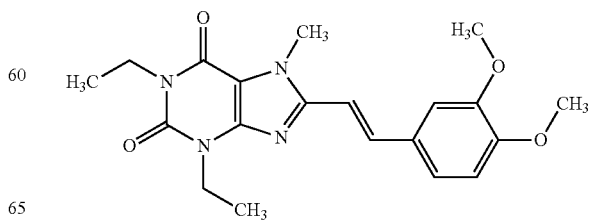

The chemical structure of ASP5854 (5-[5-amino-3-(4-fluorophenyl) pyrazin-2-yl]-1-isopropylpyridine-2(1H)-one) is as follows:

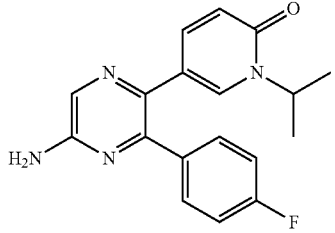 [SMILES: CC(C)n1cc(-c2ncc(N)nc2-c2ccc(F)cc2)ccc1=O]

The chemical structure of Vipadenant (BIIB014) is as follows:

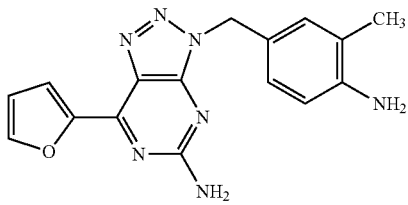 [SMILES: Cc1cc(Cn2nnc3c(-c4ccco4)nc(N)nc32)ccc1N]

The chemical structure of ST-1535 is as follows:

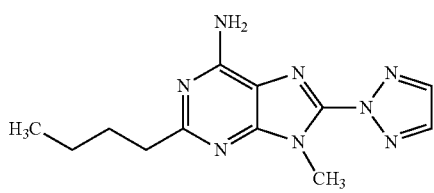 [SMILES: CCCCc1nc(N)c2nc(-n3nccn3)n(C)c2n1]

The chemical structure of Preladenant (SCH420814) is as follows:

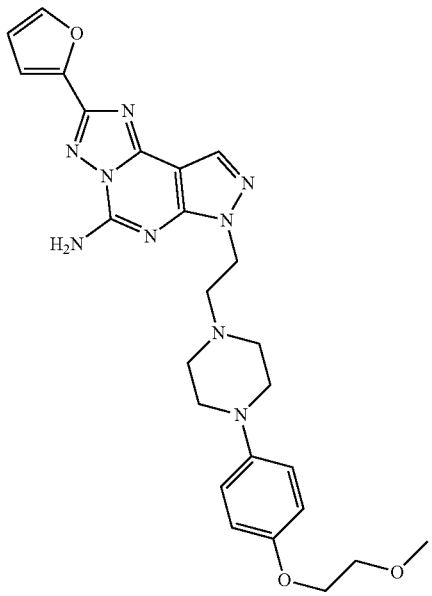 [SMILES: COCCOc1ccc(N2CCN(CCn3ncc4c3nc(N)n3nc(-c5ccco5)nc43)CC2)cc1]

The chemical structure of ZM-241,385 is as follows

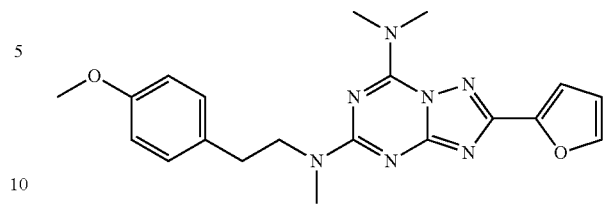

In an embodiment of the present invention the $A_{2A}$ antagonist useful in the present invention is the one of formula (I)

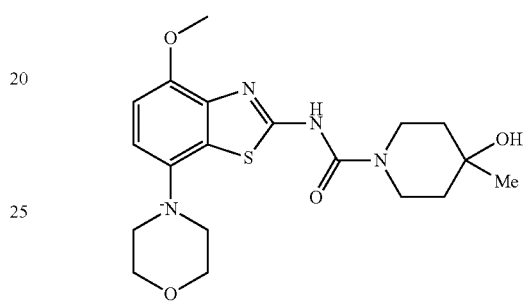

I which is 4-hydroxy-4-methyl-piperidine-1-carboxylic acid (4-methoxy-7-morpholin-4-yl-benzothiazol-2-yl)-amide, and pharmaceutically acceptable acid addition salts and co-crystals thereof.

A great variety of NR2B antagonists are known and has been claimed, e.g. in the following international patent applications, the disclosure of which is herein incorporated by reference: WO 2010/1221, WO 2009/118187, WO 2009/058261, WO 2009/025265, WO 2008/155778, WO 2007/099828, WO 2007/063839, WO 2007/063286, WO 2007/006157, WO 2006/137465, WO 2006/113471, WO 2006/017409, WO 2006/010967, WO 2006/010964, WO 2005/102390, WO 2005/080317, WO 2005/035522, WO 2005/030720, WO 2005/035523, WO 2005/019222, WO 2005/019221, WO 2004/108705, WO 2004/089366, WO 2004/048364, WO 2004/054579, WO 03/091241, WO 03/084931, WO 03/010159, WO 02/100352, WO 02/080928, WO 02/068409, WO 02/34718, WO 02/12892, WO 02/09736, WO 02/00629, WO 01/98262, WO 01/30330, WO 01/32634, WO 01/32171, WO 01/32177, WO 01/32615, WO 01/32179, WO 01/32174, WO 00/67803.

Known NR2B antagonists include the following, whereby some of them are in clinical development.

MK-0657
Traxoprodil (CP-101,606)
EVT-101
EVT-102
EVT-103

Radiprodil (RGH 896)
RG-1
ED-1529
NeurOp
NeurOp-2
NeurOp-3
NeurOp-4
TXT-0300
HON-0001
Ifenprodil
safaprodil
N-{(1S,3S)-3-[3-(4-Methylbenzyl)-1,2,4-oxadiazol-5-yl]cyclopentyl}-1H-pyrazolo[3,4-d]pyrimidin-4-amine (also designated below and in table 1 "compound 1").

The herein mentioned NR2B antagonists or $A_{2A}$ antagonists are either commercially available or may be prepared according to methodologies that are known to a person skilled in the art, including the patent references mentioned herein.

A preferred NR2B antagonist is selected from the group comprising Traxoprodil (CP-101,606), Radiprodil (RGH 896), EVT-101, EVT-102, EVT-103, Ifenprodil, MK-0657, Safaprodil or N-{(1S,3S)-3-[3-(4-Methylbenzyl)-1,2,4-oxadiazol-5-yl]cyclopentyl}-1H-pyrazolo[3,4-d]pyrimidin-4-amine named compound 1.

The chemical structure of Traxoprodil (CP-101,606) is as follows:

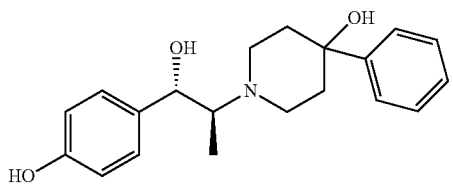 [SMILES: C[C@@H]([C@@H](O)c1ccc(O)cc1)N1CCC(O)(c2ccccc2)CC1]

The chemical structure of Radiprodil (RGH 896) is as follows

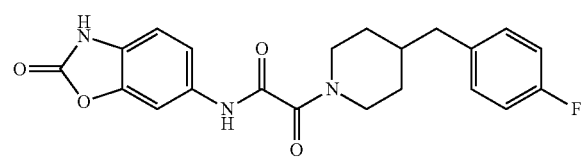 [SMILES: O=C(Nc1ccc2[nH]c(=O)oc2c1)C(=O)N1CCC(Cc2ccc(F)cc2)CC1]

The chemical structure of EVT-101 is as follows

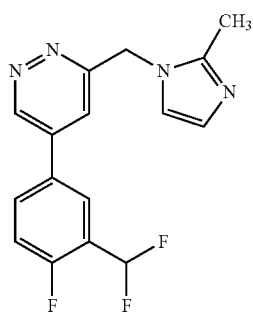 [SMILES: Cc1nccn1Cc1cc(-c2ccc(F)c(C(F)F)c2)cnn1]

The chemical structure of Ifenprodil is as follows

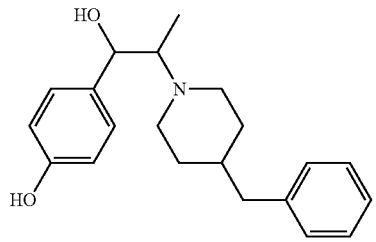 [SMILES: CC(C(O)c1ccc(O)cc1)N1CCC(Cc2ccccc2)CC1]

The chemical structure of MK-0657 is as follows

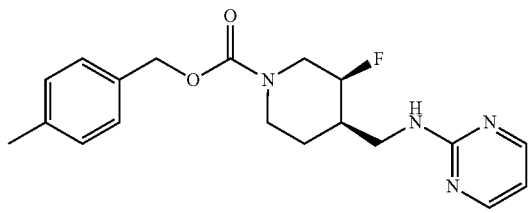 [SMILES: Cc1ccc(COC(=O)N2CC[C@H](CNc3ncccn3)[C@H](F)C2)cc1]

The chemical structure of Safaprodil is as follows:

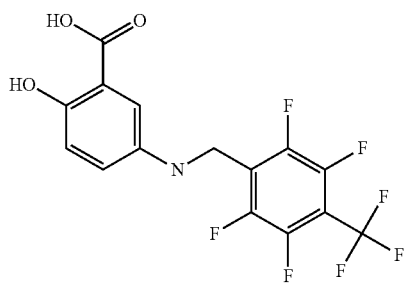 [SMILES: O=C(O)c1cc(NCc2c(F)c(F)c(C(F)(F)F)c(F)c2F)ccc1O]

The chemical structure of N-{(1S,3S)-3-[3-(4-Methylbenzyl)-1,2,4-oxadiazol-5-yl]cyclopentyl}-1 H-pyrazolo[3,4-d]pyrimidin-4-amine (compound 1) is as follow:

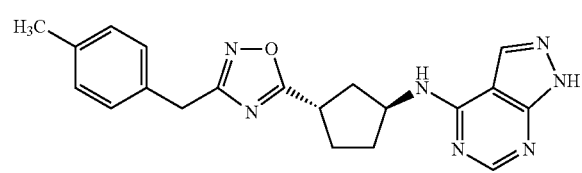 [SMILES: Cc1ccc(Cc2noc([C@H]3CC[C@H](Nc4ncnc5[nH]ncc45)C3)n2)cc1]

In an embodiment of the present invention the $A_{2A}$ antagonist is selective over each of the other adenosine receptor subtypes $A_1$, $A_{2B}$ and $A_3$ by a factor of at least 10, preferably 30 and ideally 100 or more.

In an embodiment of the present invention the NR2B antagonist is selective over each of the other NMDA receptor subtypes NR2A, NR2C, and NR2D by a factor of at least 10, preferably 30 and ideally 100 or more.

In an embodiment of the present invention the ratio of doses of the $A_{2A}$ antagonist to the NR2B antagonist varies from between 30:1 to 1:30, in another it varies from 10:1 to 1:10, in another from 3:1 to 1:3, in still another it is about 1:1.

In an embodiment of the present invention the composition comprises the combination of Radiprodil as an NR2B antagonist and Tozadenant as an $A_{2A}$ antagonist. The ratio between those two compounds may vary 30:1 to 1:30, in another it varies from 10:1 to 1:10, in another from 3:1 to 1:3.

In the method according to the present invention both pharmaceutical agents—the $A_{2A}$ antagonist and the NR2B antagonist—are administered essentially at the same time. In one embodiment they are administered at exactly the same time either alone or in combination with further pharmaceutical products for the treatment of PD.

In a further embodiment, the $A_{2A}$ antagonist and the NR2B antagonist are administered together any time once the administration of L-Dopa had started.

In a further embodiment the $A_{2A}$ antagonist and the NR2B antagonist are administered together with a dopamine agonist at any time during the treatment of the disease.

In a further embodiment the $A_{2A}$ antagonist and the NR2B antagonist are administered together with L-Dopa. L-Dopa is currently the gold standard for treating Parkinson's disease. The standard preparations (Sinemet, Atamet) combine levodopa with carbidopa, which improves the action of levodopa and reduces some of its side effects, particularly nausea. Dosages vary, although the preparation is usually taken in three or four divided doses per day.

Typical dosages of L-Dopa/carbidopa are: levodopa/carbidopa 100/25 mg 3 times/day during the early state of the disease. At later stages up to 1000 mg levodopa with 30 mg carbidopa per day can be given, although current recommendation suggests not to dose higher than 400 to 600 mg levodopa.

Further pharmaceutical products for the treatment of PD include amantadine (Symmetrel®), benztropine (Cogentin®), bromocriptine (Parlodel®), entacapone (Comtan®), pergolide (Permax®), pramipexole (Mirapex®), ropinirole (Requip®), selegiline (Eldepryl®), Sinemet® (carbidopa/levodopa), tolcapone (Tasmar®), rotigotine (Neupro®).

In one embodiment of the present invention the $A_{2A}$ antagonist and the NR2B antagonist are administered alone or together with L-Dopa once a day.

A further aspect of the present invention pertains to a pharmaceutical composition comprising a therapeutically effective amount of a combination of an adenosine $A_{2A}$ receptor antagonist and a NR2B antagonist in a pharmaceutical acceptable carrier or mixed with pharmaceutical acceptable excipients.

In an embodiment of the present invention the ratio of doses of the $A_{2A}$ antagonist to the NR2B antagonist in said pharmaceutical composition varies from between 30:1 to 1:30, in another it varies from 10:1 to 1:10, in another from 3:1 to 1:3, in still another it is about 1:1.

In an embodiment of the present invention the composition comprises the combination of Radiprodil as an NR2B antagonist and Tozadenant as an $A_{2A}$ antagonist. The ratio between those two compounds may vary 30:1 to 1:30, in another it varies from 10:1 to 1:10, in another from 3:1 to 1:3.

The pharmaceutical composition could either be a fixed combination combining both the adenosine $A_{2A}$ receptor antagonist and the NR2B antagonist in one tablet or the pharmaceutical composition could be a kit of parts.

In one embodiment of the present invention the pharmaceutical composition forms of a kit of parts comprising:
(a) a first containment containing a pharmaceutical formulation comprising a therapeutically effective amount of an $A_{2A}$ receptor antagonist, and
(b) a second containment containing a pharmaceutical formulation comprising a therapeutically effective amount of an NR2B antagonist.

The compositions according to the present invention may be used for the manufacture of a pharmaceutical composition for the treatment of Parkinson's disease. Such compositions typically contain the active pharmaceutical ingredient and a pharmaceutically acceptable excipient.

Suitable diluents and carriers may take a wide variety of forms depending on the desired route of administration, e.g., oral, rectal, parenteral or intranasal.

Pharmaceutical compositions suitable for oral administration can be solids or liquids and can, for example, be in the form of tablets, pills, dragees, gelatin capsules, solutions, syrups, chewing-gums and the like.

Pharmaceutical compositions comprising compounds according to the invention can, for example, be administered orally, parenterally, i.e., intravenously, intramuscularly or subcutaneously, intrathecally, by inhalation or intranasally.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diaminetetraacetic acid, buffers such as acetates, citrates or phosphates and agents for adjusting the osmolarity, such as sodium chloride or dextrose.

Also comprised by the present invention are pharmaceutical compositions containing the compound of the present invention in the form of a pharmaceutically acceptable cocrystal.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Preferably, the amount of each of the $A_{2A}$ antagonist and the NR2B antagonist, or its pharmaceutically acceptable salt, that is administered for the treatment of a human patient is adjusted from about 2 mg to about 200/1000 mg per day. The total daily dose may be administered as single or divided doses. Such daily treatment amount or total daily dose may be from about 5 mg to about 45 mg, from about 6 mg to about 35 mg, from about 8 mg to about 30 mg, from about 10 mg to about 25 mg, from about 12 mg to about 20 mg, from about 14 mg to about 18 mg, from about 15 mg to about 18 mg, or any range among all of the above-listed amounts. For example, the daily treatment amount is from about 2 mg, 5 mg, about 6 mg, about 8 mg, or about 10 mg to about 12 mg, about 14 mg, about 15 mg, about 16 mg, about 18 mg, about 20 mg, about 25 mg, about 30 mg, or about 35 mg. In particular, the daily treatment amount is from about 2 mg, or about 4 mg to about 20 mg, about 25 mg, or about 30 mg.

The available data would suggest that there is a co-action involved in the compositions and methods-of-use according to the present invention.

EXAMPLES

The classical motor symptoms of Parkinson's disease (PD) are associated with the loss of nigral dopaminergic cells and a decline in caudate-putamen dopamine content that led to the introduction of dopamine replacement therapy. The unilateral stereotaxic injection of 6-hydroxydopamine (6-OHDA) in to the medial forebrain bundle causes the destruction of the nigro-striatal pathway and the loss of dopaminergic input to the striatum. This model, developed in 1970 by Ungerstedt (Ungerstedt 1971; Ungerstedt and Arbuthnott 1970), mimics the status of advanced PD and is used for the testing of symptomatic drugs. The massive impairment of the dopaminergic system within one brain hemisphere creates a sensorimotor imbalance between both body sides, leading to specific behavioural deficits. Drugs stimulating postsynaptic receptor sites normally targeted by dopamine (e.g., dopamine agonists or L-Dopa) cause the rat to turn in a direction opposite to the destroyed side (contraversive rotations). This turning response is considered to be the consequence of dopaminergic receptor super-sensitivity, which follows the denervation of (parts of) the striatum (for a review, see Schwarting and Huston 1996).

The L-Dopa-induced contralateral turning response has, for a long time, represented a useful and predictive model to screen for and identify new anti-parkinsonian drugs, assessing quantitatively the effects of drugs on sensorimotor recovery.

The combined use of $A_{2A}$/NR2B antagonists relative to each of the antagonists alone has shown to provide the following surprising advantages:

Mono-treatment (administration of an NR2B/$A_{2A}$ combo alone) in drug naïve parkinsonian rats (parkinsonian rats having not received any treatment): It could be demonstrated that the efficacy on motor symptoms is comparable/essentially similar to that achieved by a fully efficacious dose of L-Dopa but unlike L-dopa, chronic combo treatment did not produce motor complications.

Mono-treatment (administration of an NR2B/$A_{2A}$ combo alone) in L-Dopa primed rats i.e rats made dyskinetic by previous L-dopa treatment the ability to fully restore motor activity in the absence of abnormal movements.

Add-on treatment to a non-active dose of L-Dopa: the combination renders efficacious a non-active dose of L-Dopa; this occurs in the absence of abnormal movements. Add-on treatment to an active dose of L-Dopa: the combination potentiates the effect of L-dopa on contralateral rotations and reduces the development of L-Do-induced-AIMs in chronic treatment (i.e. anti L-Dopa priming effect).

METHODS

Preclinical Models of Parkinson's Disease: Unilateral 6-OHDA-Lesioned Rat Model

Subjects: Males Sprague-Dawley rats (Janvier, France), weighing 250-275 g at the time of surgery and 400-450 g at the time of drug testing are used.

Upon arrival from the breeder and prior to experimentation, rats were habituated, for one week in home cages (5 rats per cage) inside the animal room. They were kept on a 12:12 light/dark cycle with light on at 06:00 h and are housed at a temperature maintained at 20-21° C. and at humidity about 40%. All animals had free access to standard pellet food and water before assignment to experimental groups.

Surgery for 6-ODHA Lesioning

On the day of surgery, one week after arrival, rats received unilateral 6-OHDA injection into the right medial forebrain bundle. Each rat was administered with Imipramine HCl (Sigma) 15 minutes before surgery to protect norepinephrinergic (NE) neurons. Rats were anesthetized with Ketamine (Ceva, 75 mg/kg) and Xylazine (Bayer, 10 mg/kg) and placed in stereotaxic frame (David Kopf Instrument). After drilling a small hole in the skull above the site of injection, 6-OHDA was injected into the right ascending medial forebrain bundle at the following coordinates (in mm) relative to bregma and surface of the dura, AP=−3.5, ML=−1.5, DV=−8.7. Each rat received one injection of 6-OHDA (4 µg/µl) for 5 minutes (0.5 µl/min) for a total of 10 µg per rat. The needle was withdrawn 4 minutes later to avoid toxin reflux. Animal were then placed in clean cages under heat source and allow to recover with food and water ad libitum. Each rat was monitored and handled regularly for 3 weeks to ensure full recovery and acclimation to the experimenters and environment.

Evaluation of the 6-OHDA Lesion

To select the successfully lesioned animals, all rats were challenged with a small dose of apomorphine (Sigma, 0.05 mg/kg, sc) on day 21 post surgery. Rats showing more than 90 contraversive rotations (360°) in a 45-min recording period were included in the study. It has been previously demonstrated that rats meeting these criterions have a unilateral loss of dopaminergic neurons and a unilateral depletion of striatal dopamine of over 95% (internal data).

Used $A_{2A}$ and NR2B Antagonists $A_{2A}$ and NR2B antagonist reference compounds were dissolved in a volume of 5 ml of vehicle per kg. L-Dopa methyl ester (Sigma) and benserazide (Sigma) were dissolved in physiological saline solution at a volume of 5 ml/kg. The vehicle solution of reference compound is made of 5% dimethyl sulfoxide (DMSO) and 95% distilled water containing 1% methyl cellulose. 6-OHDA-HBr, for the lesion, is dissolved in a 0.02% ascorbate-distilled water at a concentration of 4 µg 6-OHDA per µl.

The following $A_{2A}$ antagonists, SCH-58261 were used: Preladenant, Tozadenant and KW-6002. The NR2B antagonists used were Radiprodil, Co-101244, compound 1. The drugs were generally administered intraperitoneally, except for Tozadenant which was only administered orally. Consequently when Radiprodil was administered in combination with Tozadenant, Radiprodil was, in that case, administered orally.

Behavioural Recording Apparatus

Rotational Activity (Ipsi/Contralateral Rotations)

Rotational behaviour was recorded using a home-made computerized system. Rats were fixed in a harness, linked to mechanical sensors that were directly connected to a PC. Each 360° clock-wise or counter clock-wise turn was automatically recorded for up to 240 minutes at the maximum. Throughout the experiments, rats were allocated to individual test cages. Each of 8 clear acrylic chambers (50×40 cm), placed on a level, clear glass bottom, held by a robust frame, could be subdivided into 4 individual square test cages of 25×22 cm. A removable acrylic plate serves as a lid. A portable digital camera (Samsung, SCB-3001 PH) was positioned directly underneath each arena in order to view the whole surface covered by the chambers. This arrangement allowed the simultaneous filming of one or four rats by means of one camera, for a total of eight of thirty-two rats per session. Lighting was provided by neon-tubes fixed singularly on each leg of the frame. Video sequences were recorded on hard disk for storage and subsequently transferred to PC for analysis and conservation.

General Activity (Distance and Rearing)

General activity was recorded within large open-field measuring horizontal and vertical movements and connected to PCs. Rats were tested individually in 12 chambers (LE8811 IR, Panlab), each consisting of a square enclosure made of 0.5 cm clear acrylic sheets, without a base (45×45 cm surface×40 cm height). Each enclosure was placed on a square plate of stainless steel (inox), which served as a floor. A plastic-coated sheet was adjusted into the plate. Each apparatus was placed on a laboratory table at a 73.5 cm height. Locomotion was detected and measured by 16 infrared light-beam sensors located on each side of the enclosure at heights of 3 cm. Sensors were spaced 2.5 cm from each other and 4.0-cm from each end of the side, so that the light beams formed a matrix of 15×15 squares over the surface. Activity counts were recorded by a personal computer. The Acti-Track software (Actitrack°, Panlab) was used to convert raw data generated during the acquisition sessions into parameters statistically analyzable. The parameter "distance travelled" and "rearing counts" were kept as relevant dependent variables.

Behavioural Profile Analysis in Open-Field

The specific behavioural profile of unilateral 6-OHDA-lesioned rats was recorded via 8 cameras connected to a video acquisition system. Rats under treatment were placed freely in a small environment (rotometers, 25×22 cm) or in large open-field (50×40 cm) and the behaviour was video-recorded for 55 minutes (total of 3300 sec). The placement in the small (rotometers) or large (open-field) environment may depend on the test. The rats were filmed from below as described in the section which concerns the rotational activity.

After the in-live data recordings, the videos are subsequently analyzed by the Ethovision program from (Noldus, version 9.0). The animal and its movements and displacements were defined according to three points (nose, center and tail). The movements, position of the body and, the space occupation, were set-up according to the filter analysis defined with specific criteria and thresholds in the program. Various behavioural parameters were analyzed and only the relevant, i.e. the non-correlated ones, were kept for the final behavioural description.

The analysis of the Abnormal Involuntary movement ("AIMs") was performed with a specific parameter defined in Ethovision 9.0. The parameter "body elongation" was used to discriminate both the intensity and the frequency of dyskinetic (i.e. dystonic) position of the rat. To do so, 3 levels are determined:

"contracted"=SEVERE AIMs (threshold <30%) this parameter refers to the time spent (sec) in a position wherein the rat is on its to hindpaws (vertical up-right position with severe body truncation) and shows a very strong dystonic body position. From below, the body shape looks like a circle.

"normal"=MODERATE AIMs (threshold, 30%<Normal <50%) this parameter refers to the time spent (sec) in a the position wherein the rat is on three paws and shows a moderate dystonic position (horizontal body position with some body truncation).

"stretched"=NO AIMs (threshold >50%) this parameter refers to the time spent in a position wherein the rat is more often on four paws (horizontal position) and shows some stability without truncation of the body;

The decision for the final parameters identification and the thresholds used for the analysis were based on a first direct observation in then firmly fixed definitive analysis.

The analysis of the other types of behaviours was done with specific parameters selected in the video analysis program (Ethovision 9.0) in order to describe as best as possible the behaviour observed visually and being able to quantify it. The parameters "Distance", "Counter Clockwise rotations", "Clockwise rotations", "Streched" were extracted from the analysis. Additional parameter, the "gyration radius" is calculated from the raw data obtained by the system.

Distance (="distance"): the total distance moved by the animal (cm)

Counter clockwise (="ipsilateral turns"): count of the number of 360° turns of ipsilateral rotations in the same sense than that of the lesion.

Clockwise (="contralateral turns"): count of the number of 360° turns of contralateral rotations in the opposite sense to that of the lesion.

Stretched: (="adequate body position"): time spent in a position wherein the rat stands on its four paws without any bent position of the trunk. In the program this is the parameter "body elongation" that is used to discriminate the intensity and frequency of the adequate body position. The threshold is fixed at 70%.

Gyration Radius (="adequate trajectory"): for a specific time interval, average distance between the animal position and its average position within this specific time interval. This parameter reflect the ability of the rats to use the entire space of the arena and is measured in centimeters.

Statistical Analysis

General activity (actometers) and Rotations (rotometers): The statistical analysis for the general activity (distance and rearing) and for the rotations (contralateral) was performed by means of parametric statistics.

The level of general activity (distance and rearing) measurement in actometers was assessed by three-way mixed ANOVA with the $A_{2A}$ antagonist (2 levels) and the NR2B antagonist (2 levels) as between-group factors and the time as within-subjects factor (6 or 24 levels). Multiple pairwise comparisons among the means were performed by Tukey post hoc test.

The effects of treatment with $A_{2A}$ and/or NR2B on the levels of L-Dopa-induced contralateral rotations was evaluated with two-way mixed ANOVA with the drug treatment (4 levels) as between-group factors and the time (12 or 18 levels)

as within-subjects factor. Multiple pairwise comparisons among the means were performed by LSD post hoc test.

Data of the acquisition session under treatment with $A_{2A}$ and/or NR2B antagonist plus L-Dopa/benserazide were analyzed by two-way repeated measures ANOVA with chronic session as within-subjects factor (10 session levels). The reliabilities of the between-mean differences were assessed with planned contrasts using an F statistic. In addition, post hoc analysis was done on the variable "treatment' separately (Tukey, post hoc test).

For each test, statistical significance was assumed if P<0.05.

Specific behavioural analysis: The five behaviours kept for the thorough behavioural analysis (i.e. distance, contra turns, ipsi turns, adequate body position and adequate trajectory) were analyzed with parametric statistic however if variance homogeneity was not respected for the data (Bartlett's test for equal variances) these latter were analyzed with non-parametric statistics (Kruskal-Wallis). In both case, one-way ANOVA was performed to discriminate the effect of the various treatments on each independent behaviours. Significant differences between means were determined by Tukey post hoc test or Dunn's Multiple Comparison test with p<0.05.

LIST OF ABBREVIATIONS

Ip: intraperitoneal
Po: per os, oral adminstration
mg/kg: milligram per kilogram
sec: seconds
cm: centimeters
Rad 3: Radiprodil at the dose of 3 mg/kg
Toz 30: Tozadenant at the dose of 30 mg/kg
Combo: any combinations of $A_{2A}$ and NR2B receptor antagonist and specifically the particular
case Tozadenant 30 mg/kg+Radiprodil 3 mg/kg.
CO1: Co-101244 at the dose of 1 mg/kg
SCH1: SCH-58261 at the dose of 1 mg/kg
Veh: vehicle
LD25: L-Dopa 25 mg/kg
LD/BZ: L-Dopa plus benserazide
AIMs: Abnormal Involuntary Movements

EXPERIMENTAL SECTION

A. Monotreatment with an $A_{2a}$ Antagonist Together with an NR2B Antagonist in Hemiparkinsonian Rats Example 1

Efficacy of the Combination of an $A_{2A}$ Antagonist Together with an NR2B Antagonist on the Quantity of Activity Across Six Different Embodiments Six different co-administrations of an $A_{2A}$ antagonist together with an NR2B antagonist (=COMBO) are tested in the unilateral 6-OHDA-lesioned rat model of Parkinson's disease according to TABLE 1.

The behavioural parameters recorded were "distance travelled" and "rearing counts". These latter are automatically measured in actometers. All of the co-administrations show significant increases in the level of activity (distance and/or rearing counts) in comparison to the treatment done with the compounds alone.

TABLE 1

| | | NR2B ANTAGONIST | | |
| --- | --- | --- | --- | --- |
| | | Co-101244 | Compound 1 | Radiprodil |
| $A_{2A}$ ANTAGONIST | KW-6002 | + | | |
| | SCH-58261 | + | + | |
| | Preladenant | | + | + |
| | Tozadenant | | | + |

+: $A_{2A}$/NR2B combination tested and activity for distance and/or rearing is superior to the testing of the compounds alone In every combination (combo), the added-value of such treatment on the hemi-parkinsonian rat behaviour was remarkable and unexpected. All the combos (if adequate dose selection) were able to restore the motor function by increasing the level of activity in comparison to vehicle-treated rats and to rats treated with the compound alone. In addition, this stimulated behaviour was not associated to the typical asymmetrical behavioural bias and to the abnormal body position (i.e. dystonic body position) as is observed with current dopaminergic PD therapies (i.e. DA agonists or L-Dopa). This specific effect on the behaviour was observed visually during the testing in the actometers.

Example 2

Demonstration of the Efficacy of the Combination on the Quality of the Stimulated Motor Activity with One Specific Example (Tozadenant and Radiprodil)

The co-administration of an NR2B antagonist and an $A_{2A}$ antagonist has shown across 6 different combos an unexpected increase of the level of activity (distance travelled and rearing counts). This unexpected behavioural profile (i.e. increase motor activity with excellent body position) that was observed visually while the animals were placed in the activity chambers (actometers) is described, in detail, in the subsequent example and illustrated by the quantitative measurement of various behavioural parameters.

The effects of the oral co-administration of Radiprodil (3 mg/kg, po) with Tozadenant (30 mg/kg, po) on the rat behaviour are compared to the testing of:
1) these compounds separately
2) a partially active dose of L-Dopa (25 mg/kg, ip)
3) a fully active dose of L-Dopa/benserazide (16/4 mg/kg, ip).

The behavioural profile was analyzed in detail with an automated behavioural analysis system based on video recordings (see methods section for the description). In addition, classical measurements (rotometers and actometers) of the behaviour are also used to assess quantity of movements. Movement Quantity Analysis: Length of the Stimulated Effect When tested in an automated apparatus, the combo showed a long-lasting effect whereas an active dose of L-Dopa/benserazide lasted for about 3 hours and a partially active dose lasted about one hour (very short acting efficacy). In the experiment with the combo, rats were put in the testing arena 60 minutes after the oral administration of the compounds (i.e. Tozadenant and/or Radiprodil) whereas rats which received L-Dopa 25 mg/kg were put in the rotometers 10 min after the L-Dopa administration (ip) and rats treatment with L-Dopa/benserazide, 15 min after the intraperitoneal administration.

The data in FIG. 2 (i.e. comparison of vehicle, L-Dopa 25 and L-Dopa/benserazide groups) come from different experiments and were grouped together for subsequent analysis.

FIG. 1:

Right graph: Three-way mixed ANOVA. Significant effect of Radiprodil (3 mg/kg), $F(1,28)=51.45$, $p<0.001$. Significant effect of Tozadenant (30 mg/kg), $F(1,28)=176.0$, $p<0.001$. Significant effect of time, $F(23,644)=42.28$, $p<0.001$. Significant « Radiprodil×Tozadenant » interaction, $F(1,28)=14.81$, $p<0.01$.

Tukey post hoc test ($p<0.05$): rats treated with the TOZ 30/RAD 3 combination have higher score of distance than those from the VEH/VEH, TOZ 30/VEH and VEH/RAD 3 groups.

Left graph: Three-way mixed ANOVA. Significant effect of Radiprodil (3 mg/kg), $F(1,28)=9.40$, $p<0.01$. Significant effect of Tozadenant (30 mg/kg), $F(1,28)=64.60$, $p<0.001$. Significant effect of time, $F(23,644)=16.67$, $p<0.001$. Significant « Radiprodil×Tozadenant » interaction, $F(1,28)=4.60$, $p<0.05$.

Tukey post hoc test ($p<0.05$): rats treated with the TOZ 30/RAD 3 combination have higher score of rearing than those from the VEH/VEH, TOZ 30/VEH and VEH/RAD 3 groups.

FIG. 2:

The effect of treatment shows significant effect $F(2,21)=43.68$, $p<0.001$. Significant effect of time is also observed $F(17,357)=20.05$, $p<0.001$ and significant interaction as well $F(34,357)=11.74$, $p<0.001$. Additional post hoc comparisons test shows that this is only the effect with L-Dopa/benserazide which is significantly active in comparison to vehicle-treated rats (Tukey, $p<0.05$).

Movement Quality Analysis: Detailed Quantification and Qualification of Various Types of Behaviours Thorough behavioural analysis showed that the combo has an unexpected effect on the behaviour of the hemiparkinsonian rats: the combination of Radiprodil and Tozadenant (i.e "Combo") restores the quantity of movement comparable to that observed with an active dose of L-Dopa/benserazide (which is not the case with the compound tested separately). In addition, this combo also offers a strong improvement of the quality of the behaviour. The direction, the trajectory and the body position are noticeably improved and correspond to behaviours observed in non-lesioned rats.

Typically, L-Dopa-treated rats show (1) stereotypic contralateral rotations (full incapacity to shift from contra to ipsilateral direction), (2) a bent body position and, (3) a trajectory (gyration radius) of the displacement which is very short since they only do tight contralateral rotations while stimulated.

By contrast, the combo treated rats show (1) the ability to shift from the contra to the ipsilateral direction, (2) no bent body position (adequate body position if reference to the position of a non-lesioned rat which stands well on its four paws without any distortion of the trunk) and, (3) trajectory which is larger since they move straight and do not display any tight stereotypic contralateral rotations like those typically observed under L-Dopa.

TABLE 2: divided in three behavioural categories (1) quantity of movement, (2) Ability to shift the direction, (3) Trajectory and body position, compares the effects of Radiprodil and Tozadenant alone, the combo made of "Tozadenant+Radiprodil", and a partially active dose of L-Dopa (25 mg/kg) and a significant active dose of L-Dopa/benserazide (16/4 mg/kg). The results represent the percentage of change in comparison to vehicle-treated hemi-parkinsonian rats; the objective being to measure the index of recovery. Those data are expressed for two different time points of the test.

This table shows that the quantity of movements (distance) of the combo-treated rats is highly superior to that observed with the vehicle-treated rats and this effect is comparable to that produced by L-Dopa/Benserazide-treated rats. By contrast, the percentage of "adequate body position" and the "adequate trajectory" are highly increased with the combo in comparison to the testing of the compounds alone, the vehicle and the L-Dopa/Benserazide-treated group. The L-Dopa/benserazide group also shows a strong bias towards the contralateral side in comparison to the vehicle-treated rats. Such a bias is not observed with the combo or with the compounds alone.

TABLE 2

| | TIME | Radiprodil | Tozadenant | Combo | LD25 | LD/BZ |
|---|---|---|---|---|---|---|
| Quantity of movement | | | | | | |
| Distance | 0-20' | ++ | + | +++ | ++ | +++ |
| | 30-50' | + | ++ | ++++ | +++ | ++++ |
| Ability to shift direction | | | | | | |
| Contra turns | 0-20' | + | + | ++ | +++ | ++++ |
| | 30-50' | + | ++ | ++++ | +++ | ++++ |
| Ipis turns | 0-20' | + | + | ++ | ++ | − |
| | 30-50' | + | ++ | +++ | ++ | − |
| Body position and trajectory | | | | | | |
| Adequate body position | 0-20' | ++ | + | ++ | + | − |
| | 30-50' | ++ | ++ | +++ | ++ | − |
| Adequate trajectory | 0-20' | ++ | +++ | ++++ | +++ | +++ |
| | 30-50' | ++ | +++ | ++++ | +++ | +++ |
| Expressed as % of the veh-treated rats | <200% | − | | | | |
| | 200-300% | + | | | | |
| | 300-500% | ++ | | | | |
| | >500% | +++ | | | | |
| | >1000% | ++++ | | | | |

FIG. 3 shows the ability of the combo to produce equivalent quantity of movements (distance) to that observed with L-Dopa/benserazide-treated rats for the first 20 minutes and the last 20 minutes of the test.

FIG. 4 shows the ability of the combo to induce both ipsi and contralateral turns (movements) whereas L-Dopa/benserazide-treated rats only show the ability to go towards the contralateral side. This observation clearly demonstrated the (1) ability of rats under combo to be able to shift from one direction to the other while being stimulated and (2) absence of major contralateral rotational activity of the combo-treated rats when these are stimulated.

FIG. 5 demonstrates the improvement of both the trajectory and the body position in the combo-treated rats in comparison to rats treated with L-Dopa/benserazide. Indeed, the trajectory measured through the gyration radius is higher in combo treated rats during the two time periods of the recordings than that observed with the other groups. This observation reflects quantitatively that whilst stimulated, rats treated with the combo have larger trajectories in the testing arena than the L-Dopa/benserazide treated rats which execute very tight movements during their contralateral rotations. The body position of the rats under the combo shows that even if those rats are stimulated by the treatment, they can stand on their four paws and do not have a bent position.

These unexpected observations and description demonstrate that, with combination treatment it is possible to achieve an equivalent level of stimulation without the abnormal motor complications which are typically associated with the dopaminergic therapy in unilateral 6-OHDA-lesioned rats.

Example 3

Efficacy of the Combined Administration of "Tozadenant+Radiprodil" on Motor Symptoms without the Development of any Abnormal Movements after Chronic Treatment Chronic treatment for 10 days with the combo does not lead to the development of any abnormal motor complications as is observed with L-Dopa. The rats remain active even if some habituation process develop to the testing arena. Despite this normal phenomenon, the significant effect of the combo on the level of activity and on the quality of the movement is still observed.

Example 4

Efficacy of the Combo on Motor Symptoms on Hemi-Parkinsonian Rats which Had been Previously Made Fully Dyskinetic by Prior Chronic Treatment with L-Dopa The combined administration of "Tozadenant+Radiprodil" has the capacity to restore increased motor activity in hemi-parkinsonian rats. However, this specific co-administration has also the entirely unexpected effect since it restores motor activity without abnormal involuntary movements in hemi-parkinsonian L-Dopa-primed rats which were rendered fully dyskinetic with a chronic L-Dopa treatment.

Hemi-parkinsonian rats treated for 10 acquisition sessions under L-Dopa 14 mg/kg and benserazide 3.5 mg/kg develop an increased level of both contralateral rotations and severe Abnormal Involuntary Movements (AIMs) (i.e. behavioural sensitization). Consecutively to that chronic L-Dopa/benzerazide treatment, they show a very high level of contralateral rotations and AIMs at the end of this chronic treatment when tested in the open-field. When these highly dyskinetic hemi-parkinsonian rats were taken off L-Dopa and treated with the combo some days later (e.g. after 3 days), we observe full restoration of the adequate motor activity without any abnormal involuntary movements or without any increase of the level of contralateral rotations. This absence of cross-sensitization on the level of contralateral rotations and AIMs result was entirely unexpected.

Table 3 shows, for seven behaviours, the percentage of change expressed by the rats when treated with vehicle, Radiprodil 3 mg/kg, Tozadenant 30 mg/kg or the combo in comparison to the respective behaviours displayed by the same rats but when these latter were treated with an active dose of L-Dopa/benserazide some days earlier.

Table 3 shows, for combo-treated rats:

(1) comparable level of distance travelled to those treated with L-Dopa/benserazide whereas rats treated with the compounds alone showed a decreased level of activity;

(2) a reduction of L-Dopa-induced contralateral rotations and an increase of ipsilateral rotations in comparison to rats treated with L-Dopa/benserazide;

(3) an increase of the time spent in the adequate body position and improved trajectory in comparison to rats treated with L-Dopa/benserazide (4) no time spent in displaying Abnormal Involuntary Movements (AIMs) in comparison to rats treated with L-Dopa/benserazide.

Figure 6:
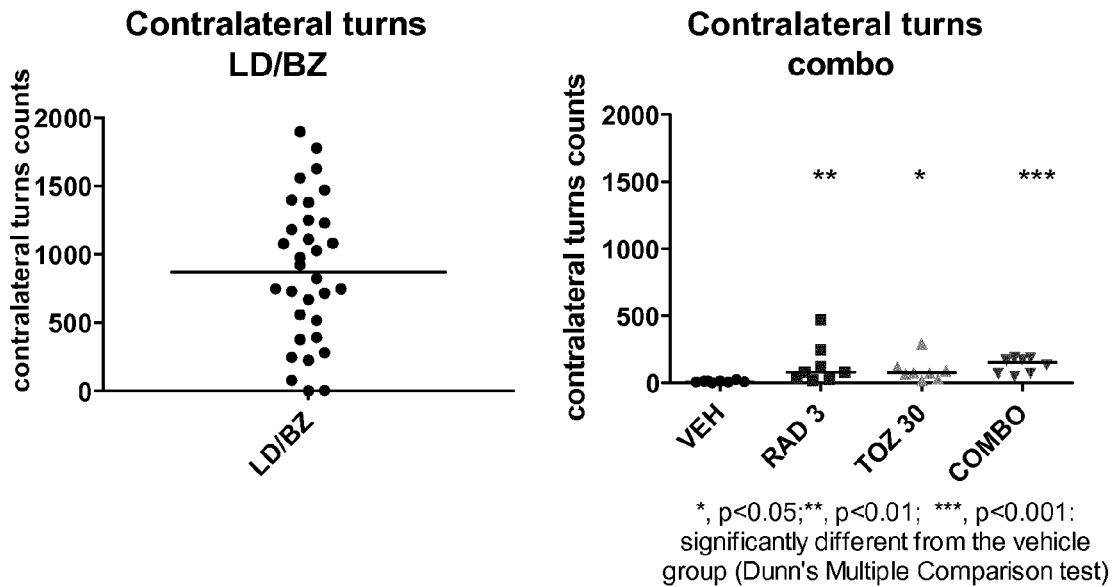
Figure 7:
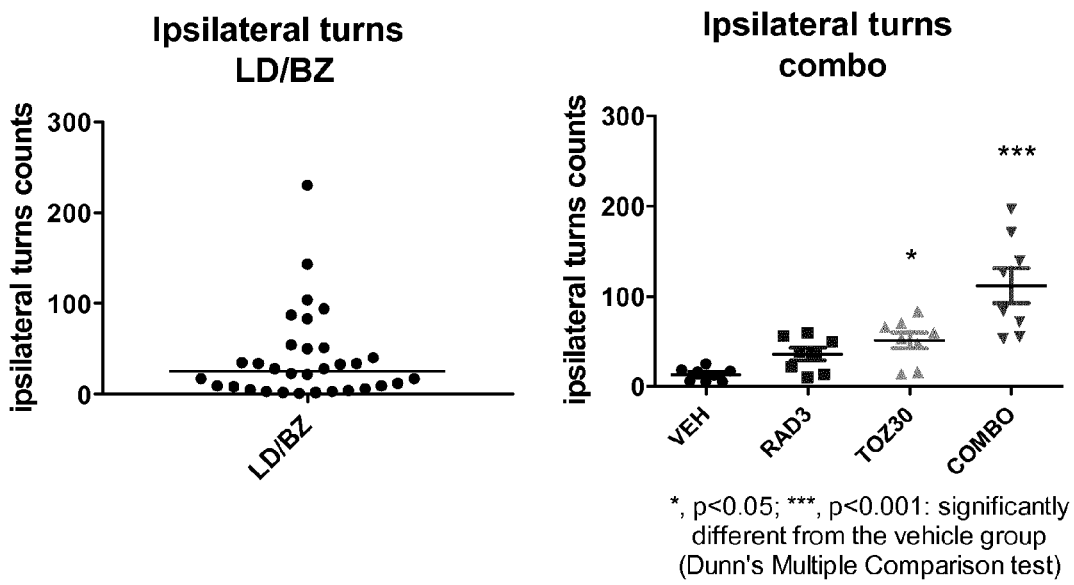
Figure 8:
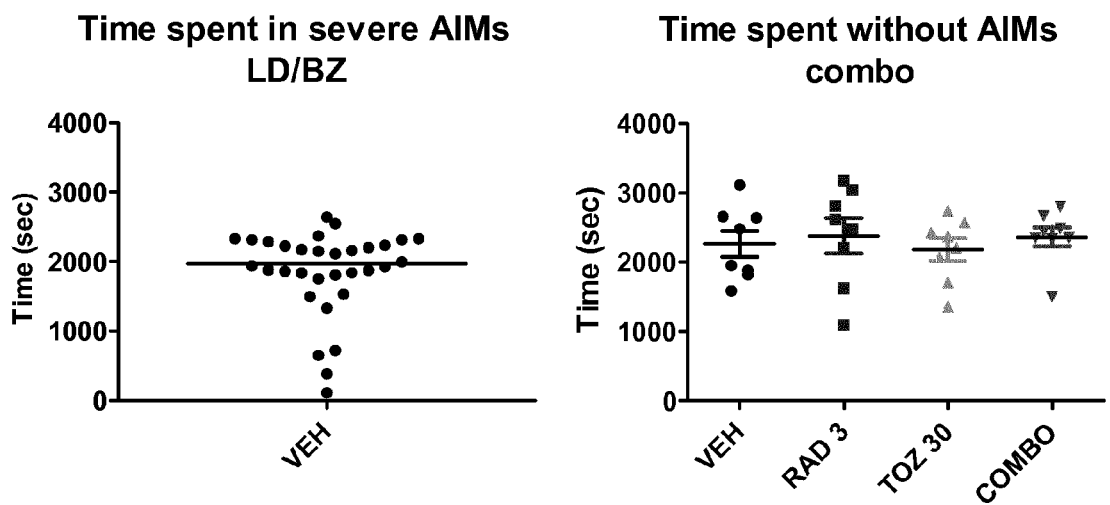
Figure 9:
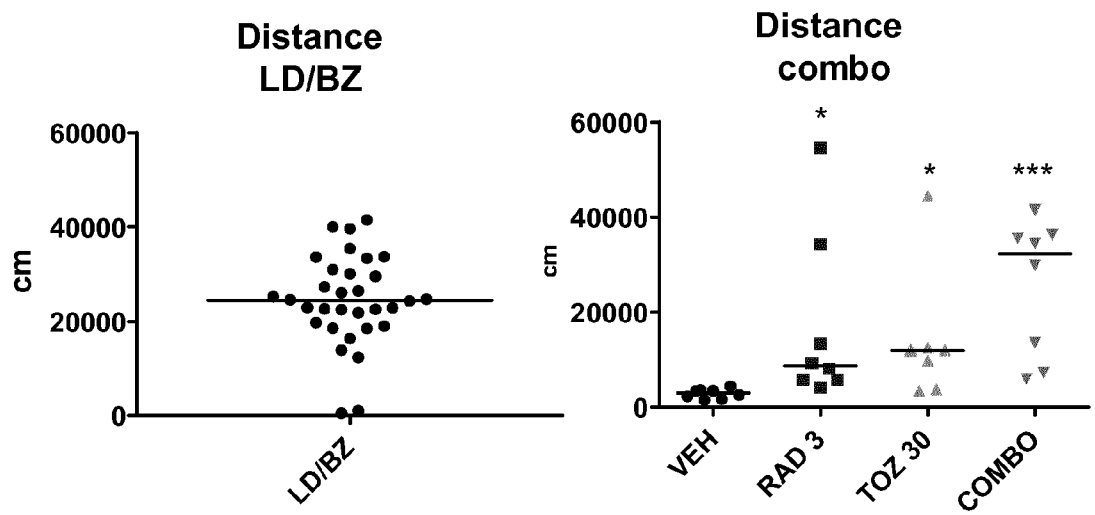
Figure 10:
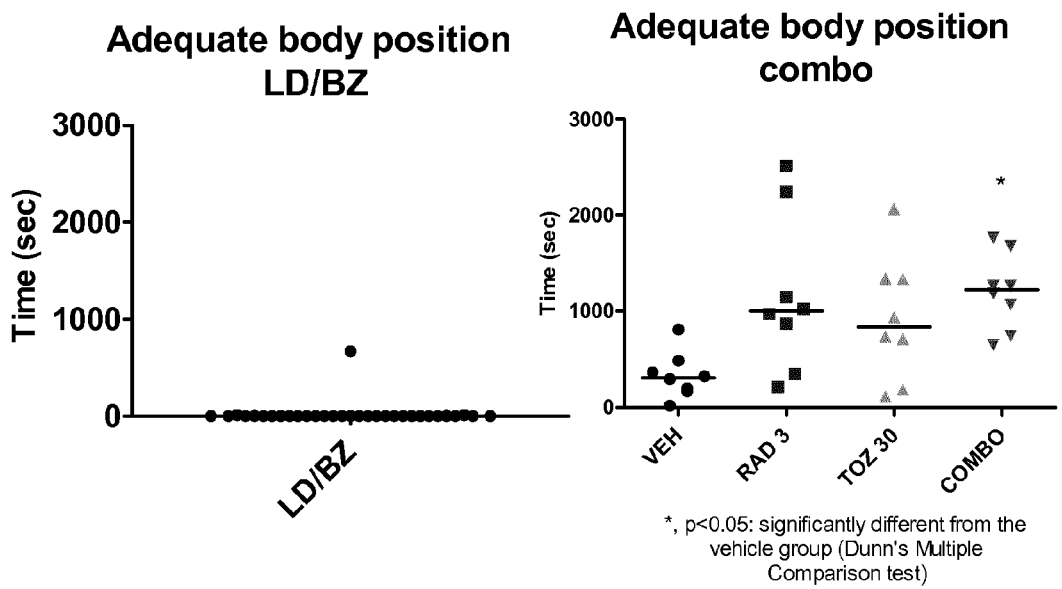
Figure 11:
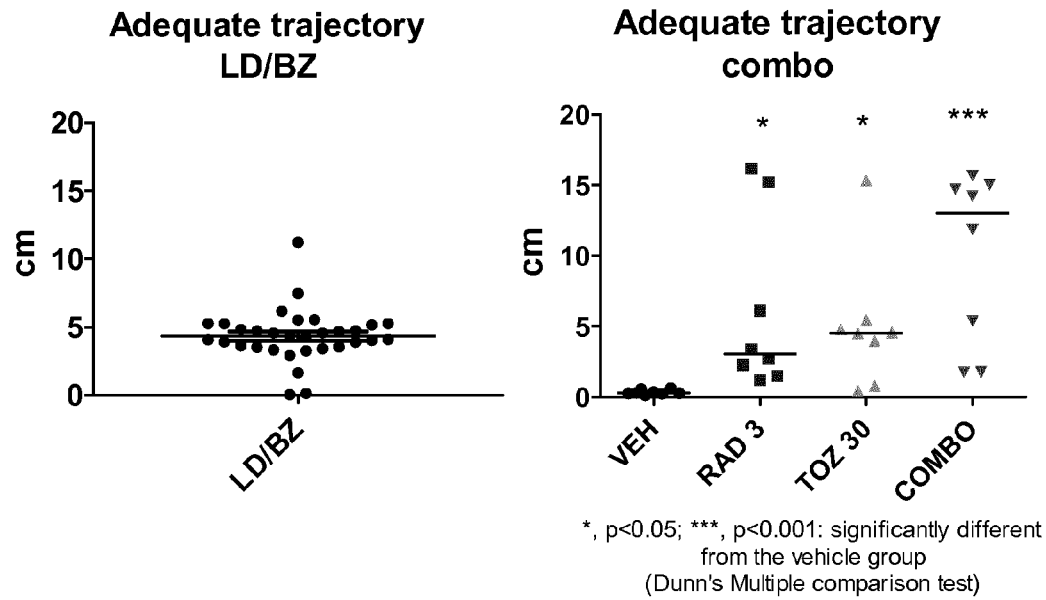

FIGS. 6 and 7 show that rats treated with L-Dopa/benserazide for 10 acquisition sessions display a strong increase of the level of contralateral turns (which is expected under L-Dopa/benserazide) and no ipsilateral turns whereas under combo those rats only express lower level of contralateral turns and some level of ipsilateral turns. This latter observation demonstrates that stimulated rats under combo are able to shift from one direction to the other. In parallel to the strong increase of contralateral rotations, rats under L-Dopa have a strong increase of the time spent in severe AIMs whereas once under the combo, the majority of the time spent by those rats is in the "no AIMs" position (FIG. 8). L-Dopa/benserazide treatment highly stimulates the rats. Observation which is reflected through the high level of distance travelled measured in those rats. However rats under the combo show equivalent level of distance travelled than those measured under L-Dopa/benserazide (FIG. 9). This showed that the combo effect, even if it does not induce any contralateral rotations itself, has still the capacity to stimulate the animals. Very interestingly, the rats stimulated with the combo spend more time in "adequate body position" in comparison to when treated with L-Dopa/benserazide (FIG. 10). The combo-treated rats also show a by far better space occupation and trajectory in comparison to the treatment under L-Dopa/benserazide since the gyration radius of their movement is increased in comparison to when they were treated with L-Dopa/benserazide (FIG. 11).

TABLE 3

|  | Vehicle | Radiprodil 3 mg/kg | Tozadenant 30 mg/kg | Combo (Toz 30 + Rad 3) |
|---|---|---|---|---|
| Quantity of movement |  |  |  |  |
| Distance Ability to shift direction | 12% ↓ | 69% ↓ | 56% ↓ | 105% ↔ |
| Contra turns | 1% ↓ | 16% ↓ | 11% ↓ | 15% ↓ |
| Ipsi turns | 33% ↓ | 91% ↔ | 130% ↔ | 283% ↑ |
| Body position and trajectory |  |  |  |  |
| Adequate body position | 1480% ↑ | 5236% ↑ | 4151% ↑ | 5391% ↑ |

TABLE 3-continued

|  | Vehicle | Radiprodil 3 mg/kg | Tozadenant 30 mg/kg | Combo (Toz 30 + Rad 3) |
|---|---|---|---|---|
| Adequate trajectory Abnormal Involuntary Movements | 8% ↓ | 140% ↑ | 114% ↔ | 231% ↑ |
| Severe AIMs | 10% ↓ | 7% ↓ | 12% ↓ | 16% ↓ |
| No AIMs | 984% ↑ | 1035% ↑ | 948% ↑ | 1029% ↑ |

↑ behavior increase in comparison to while treated under LD/BZ
↓ behavior decrease in comparison to while treated under LD/BZ
↔ no behavioral change in comparison to while treated under LD/BZ B. Add-on Treatment with an $A_{2a}$ Antagonist Together with an NR2B Antagonist in Hemiparkinsonian Rats Example 5

Behavioural Observation when Given in Acute Add-on Treatment to a Sub-Active or Partially Active Dose of L-Dopa The combined administration of an NR2B antagonist to an $A_{2A}$ antagonist potentiates the efficacy of a sub or partially active dose of L-Dopa in comparison to the compounds tested separately.

CO-101244+SCH-58261+Subactive Dose of L-Dopa

The co-administration of 1 mg/kg of Co-101244 to 1 mg/kg of SCH-58261 given as add-on treatment to a sub-active active dose of L-Dopa (15 mg/kg) significantly increases the level of contralateral rotations in comparison to vehicle-treated rats and to rats treated with the compounds alone, all groups being treated with L-Dopa 15 mg/kg.

Figure 12:
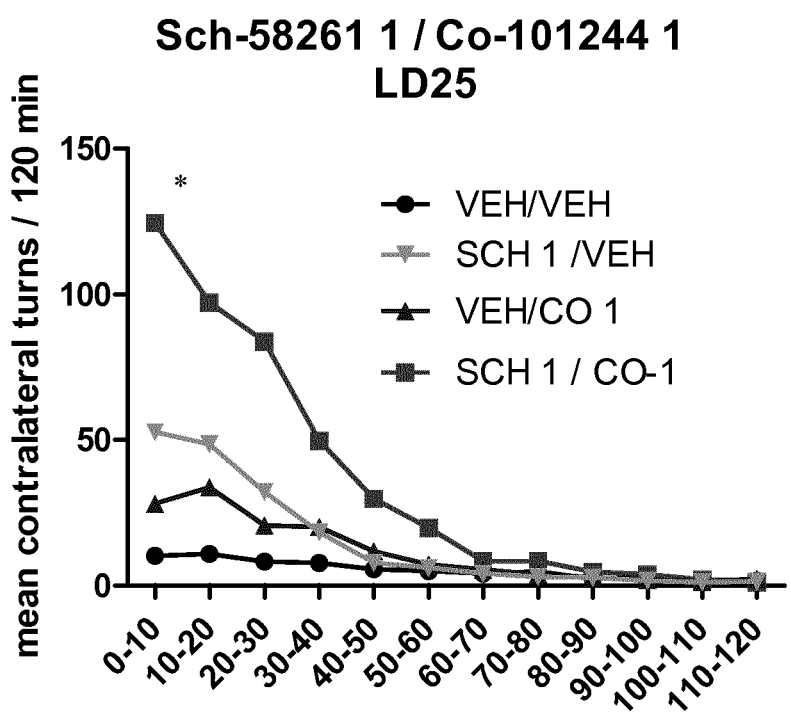

FIG. 12: Two-way ANOVA shows significant effect of treatment (F3,28)=5.62, p<0.01, significant effect of time (11,308)=22.21, p<0.001 and significant treatment×time interaction (F33,308)=4.71, p<0.001. *, p<0.05: SCH1/CO1 is significantly different from the groups VEH/VEH, SCH1/VEH and VEH/CO1 (LSD post hoc test).

Tozadenant+Radiprodil+Partially Active Dose of L-Dopa

The combined administration of 3 mg/kg of Radiprodil to 30 mg/kg of Tozadenant given as add-on treatment to a partially active dose of L-Dopa (25 mg/kg) significantly increases the level of contralateral rotations in comparison to vehicle-treated rats and to rats treated with the compounds alone in addition to L-Dopa 25 mg/kg.

Figure 13:
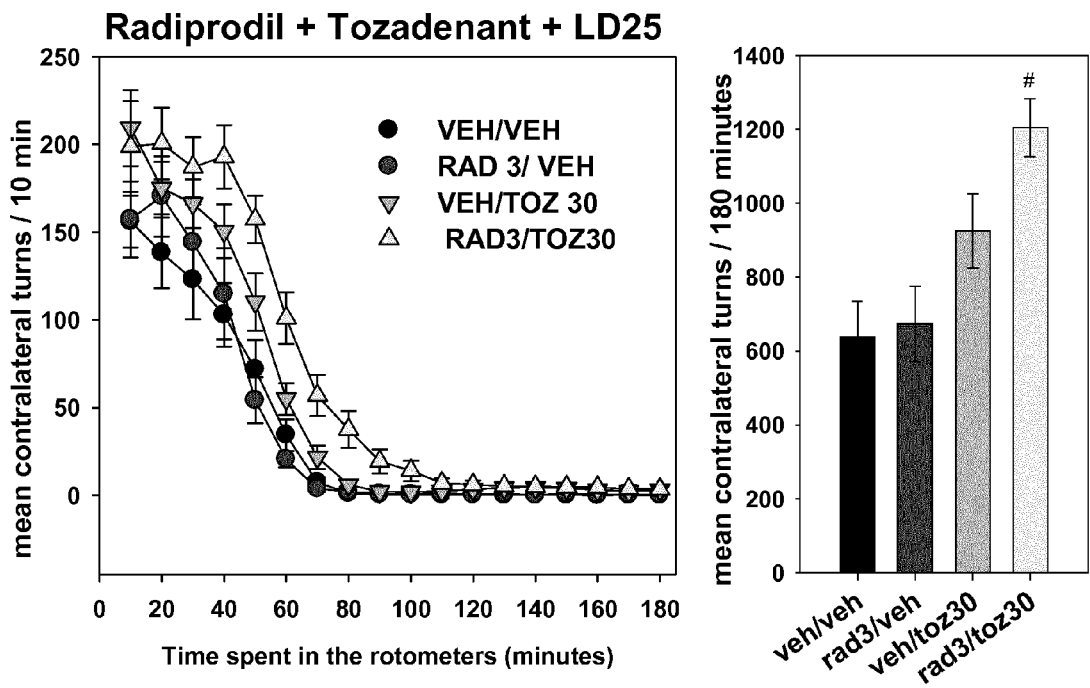

FIG. 13: Significant effect of treatment (F3,28)=70.60, p<0.01, significant effect of time (17,746)=200.89, p<0.001 and significant treatment×time interaction (F17,476)=2.83, p<0.001. #, p<0.05: The group RAD3/TOZ30 is significantly different from the groups VEH/VEH, VEH/TOZ30 and RAD3/VEH (LSD post hoc test).

Example 6

Behavioural Observation when Given in Chronic Add-on Treatment to an Active Dose of L-Dopa and Benserazide As unexpected observation, the data showed that the combo has the potential to increase the on-time effect of L-Dopa with reduction of some motor disabilities.

The chronic combined "Tozadenant+Radiprodil" administration given in add-on therapy to an active dose of L-Dopa/benserazide significantly increases the effect of L-Dopa on contralateral rotations in comparison to vehicle-treated rats and to rats treated with the single compounds. In addition to that increased effect, the testing in larger open-field showed that the level of severe AIMs is reduced with rats treated with the combo and Radiprodil in comparison to rats treated with Tozadenant.

Tozadenant+Radiprodil+Active Dose of L-Dopa/Benserazide

FIG. 14: Experimental design for the combination Tozadenant+Radiprodil administration with an active dose of L-Dopa/Benserazide

TABLE 4

Treatments administered for the 10 acquisition sessions in small rotometers.

| Groups | Treatment 1 | Treatment 2 | L- Dopa/benserazide |
|---|---|---|---|
| 1 | Vehicle | Vehicle | L-Dopa 14 mg/kg/BZ 3.5 mg/kg |
| 2 | Rad 3 mg/Kg | vehicle | L-Dopa 14 mg/kg/BZ 3.5 mg/kg |
| 3 | Vehicle | Toz 30 mg/kg | L-Dopa 14 mg/kg/BZ 3.5 mg/kg |
| 4 | Rad 3 mg/Kg | Toz 30 mg/kg | L-Dopa 14 mg/kg/BZ 3.5 mg/kg |

Figure 15:
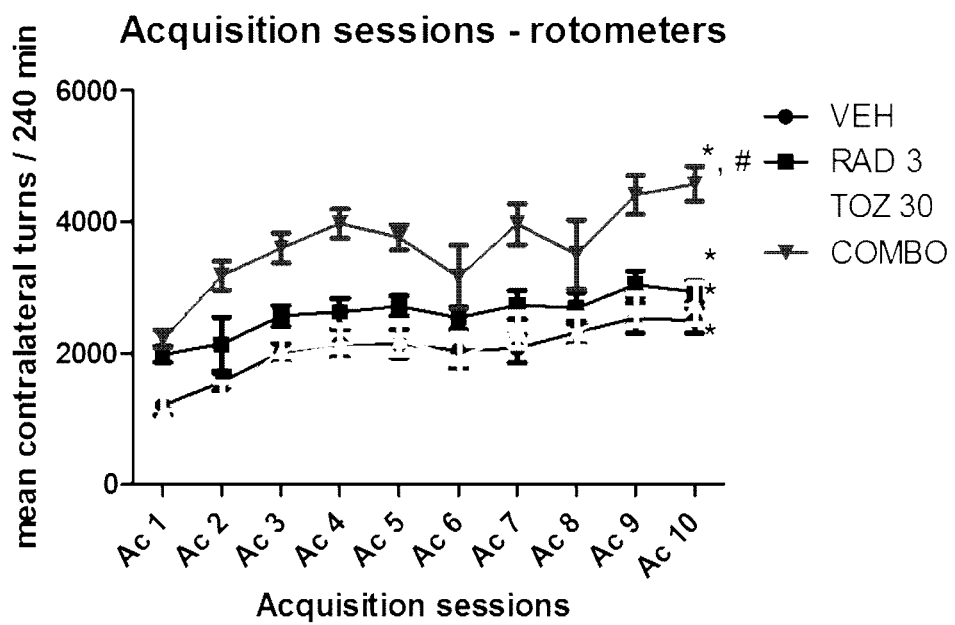
Figure 16:
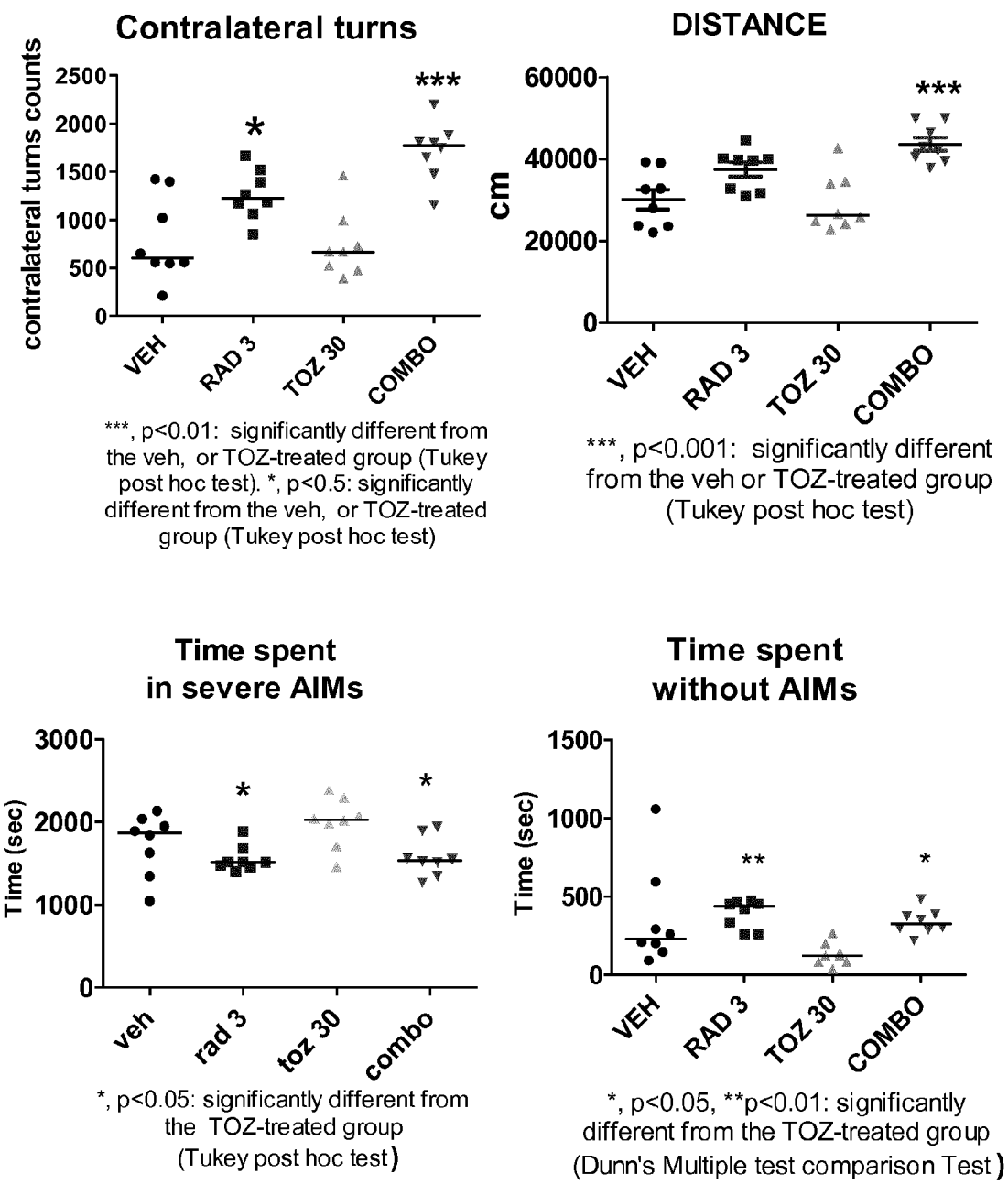

Ten acquisition sessions (once/day) of L-Dopa (14 mg/kg)/benserazide (3.5 mg/kg) given in co-administration to veh, Tozadenant, Radiprodil or the combination of both compounds increase progressively the level of L-Dopa-induced contralateral rotations when measured in rotometers (FIG. 15). The effect being more pronounced with the combo-treated rats. FIG. 16 shows the behavioural profile of rats treated with veh, radiprodil, tozadenant or the combo and L-Dopa/benserazide but when tested in larger open-field. Distinctive automated behavioural analysis based, on the video recording shows that rats treated with the combo in addition to L-Dopa/benserazide have higher level of stimulation (i.e. measured by significant increase of the level of distance and contralateral rotations). However, those rats, treated with combo and LD/BZ also showed less time spent in expressing severe AIMs than the Tozadenant-treated group.

FIG. 15: Two-way mixed ANOVA shows significant effect of treatment F(3,28)=15.06; p<0.001, significant effect of the acquisition session, F(9,252)=29.23, p<0.001 but no treatment×time interaction (p=0.18). Additional post hoc test showed that the combo group has significant higher level of activity in comparison to the veh-, toz- and rad-treated groups (Tukey, p<0.05).

In summary, the following surprising co-actions were identified:

1) Six different combinations (combos) made by combining various $A_{2A}$ and NR2B antagonists show significant increases in the level of activity (distance travelled and rearing) in unilateral 6-OHDA-lesioned rats in comparison to vehicle-treated rats and to rats treated with $A_{2A}$ antagonist or NR2B antagonist alone.

2) Thorough behavioural analysis, performed on one specific $A_{2A}$/NR2B antagonist combination (Tozadenant+Radiprodil), shows that besides the significant increase of the level of activity which is comparable to that observed with an active dose of L-Dopa/benserazide, the rats behaviour under combo is significantly improved in comparison to that observed under L-Dopa treatment (no stereotypic tight contralateral rotation and no dystonic body position).

3) Chronic treatment with the combination of an $A_{2A}$ and an NR2B antagonist does not lead to the development of any abnormal motor complications.
4) Absence of cross-sensitization effect between L-Dopa and the combo: acute treatment with the $A_{2A}$/NR2B combination in chronically L-Dopa treated rats rendered dyskinetic by the L-Dopa-treatment show the ability to restore high quality motor activity without any abnormal involuntary movement.
5) Acute treatment with the combination of $A_{2A}$ and NR2B antagonists shows significant increase of L-Dopa-induced contralateral rotations when this is given in co-administration to a sub-active or a partially active dose of L-Dopa in comparison to vehicle-treated rats or to rats treated with the $A_{2A}$ or the NR2B antagonist alone and plus the equivalent dose of L-Dopa to that received but the combo group.
6) Chronic treatment with $A_{2A}$ and NR2B antagonists given in co-administration to an active dose of L-Dopa/benserazide (dose responsible for the development of L-Dopa-induced Abnormal Movements AIMs) shows a potentiation of the L-Dopa effect on the level of contralateral rotations and, at the same time, a reduction of the severity of AIMs in comparison to rats treated with the $A_{2A}$ antagonist.

REFERENCES

Schwarting R K, Huston J P (1996) The unilateral 6-hydroxy-dopamine lesion model in behavioural brain research. Analysis of functional deficits, recovery and treatments. Prog Neurobiol 50:275-331

Ungerstedt U (1971) Postsynaptic supersensitivity after 6-hydroxy-dopamine induced degeneration of the nigro-striatal dopamine system. Acta Physiol Scand Suppl 367:69-93

Ungerstedt U, Arbuthnott G W (1970) Quantitative recording of rotational behaviour in rats after 6-hydroxy-dopamine lesions of the nigrostriatal dopamine system. Brain Res 24:485-493

Loftis J M, Janowsky A (2003) The N-methyl-D-aspartate receptor subunit NR2B: localization, functional properties, regulation and clinical implications. Pharmacol. Ther. 97:55-85.

Warraich S T, Allbutt H N, Biling R, Radford J, Coster M J, Kassiou M, Henderson J M (2009) Evaluation of behavioural effects of a selective NMDA NR1A/2B receptor antagonist in the unilateral 6-OHDA lesion rat model. Bull Res Bull. 78 (2-3):85-90

Hallett P J, Standaert D G (2004) Rationale for and use of NMDA receptor antagonists in Parkinson's disease. Pharmacol. Ther. 102:155-174

Nash J E, Fox S H, Henry B, Hill M P, Peggs D, McGuire S, Maneuf Y, Hille C, Brotchie J M, Crossman A R (2000) Antiparkinson actions of Ifenprodil in the MPTP-lesioned marmoset model of Parkinson's disease. Experiment Neurol. 165:136-142

Xu K, Bastia E, Schwarzschild M (2005) Therapeutic potential of adenosine $A_{2A}$ receptor antagonists in Parkinson's disease. Pharmacol Ther 105: 267-310

Jenner P, (2003) $A_{2A}$ antagonists as novel non dopaminergic therapy for motor dysfunction in P D. Neurol. 9; 61 (11 Suppl6):532-8.

Schiffmann S N, Fisone G, Moresco R, Cunha R A, Ferre S (2007) Adenosine $A_{2A}$ receptors and basal ganglia physiology.

Bibbiani, F. et al. Combined blockade of AMPA and NMDA glutamate receptors reduces levodopa-induced motor complications in animal models of PD. Exp. Neurol. 196, 422-429 (2005).

Blanchet, P. J., Konitsiotis, S. & Chase, T. N. Amantadine reduces levodopa-induced dyskinesias in parkinsonian monkeys. Mov. Disord. 13, 798-802 (1998).

Chase, T. N., Oh, J. D. and Konitsiotis, S. Antiparkinsonian and antidyskinetic activity of drugs targeting central glutamatergic mechanisms. J. Neurol. 247 (Suppl. 2), 1136-1142 (2000).

Delfino M A, Stefano A V, Ferrario J E, Taravini I R, Murer M G, Gershanik O S. Behaviour Behavioural sensitization to different dopamine agonists in a parkinsonian rodent model of drug-induced dyskinesias. Behav Brain Res. 2004 Jul. 9; 152(2):297-30

Mizuno Y, Hasegawa K, Kondo T, Kuno S, Yamamoto M; Japanese Istradefylline Study Group. Clinical efficacy of istradefylline (KW-6002) in Parkinson's disease: a randomized, controlled study. Mov Disord. 2010 Jul. 30; 25(10):1437-43

Morelli M, Di Chiara G. Agonist-induced homologous and heterologous sensitization to D-1- and D-2-dependent contraversive turning. Eur J Pharmacol. 1987 Sep. 2; 141(1): 101-7.

Nutt J G, Gunzler S A, Kirchhoff T, Hogarth P, Weaver J L, Krams M, Jamerson B, Menniti F S, Landen J W. Effects of a NR2B selective NMDA glutamate antagonist, CP-101, 606, on dyskinesia and Parkinsonism. Mov Disord. 2008 Oct. 15; 23(13):1860-6.

Yu L, Schwarzschild M A, Chen J F. Cross-sensitization between caffeine- and L-dopa-induced behaviours in hemiparkinsonian mice. Neurosci Lett. 2006 Jan. 23; 393 (1):31-5.

Hauber W, Münkle M. The adenosine receptor antagonist theophylline induces a monoamine-dependent increase of the anticataleptic effects of NMDA receptor antagonists. Naunyn Schmiedebergs Arch Pharmacol. 1996 July; 354 (2):179-86

Hauber W, Münkle M. Motor depressant effects mediated by dopamine D2 and adenosine $A_{2A}$ receptors in the nucleus accumbens and the caudate-putamen. Eur J Pharmacol. 1997 Apr. 4; 323(2-3):127-31.

The invention claimed is:

1. A pharmaceutical composition comprising a therapeutically effective amount of a combination of the pharmaceutical agents 4-hydroxy-N-(4-methoxy-7-morpholin-4-yl-1,3-benzothiazol-2-yl)-4-methylpiperidine-1-carboxamide (TOZADENANT®) and 2-[4-[(4-fluorophenyl)methyl]piperidin-1-yl]-2-oxo-N-(2-oxo-3H-1,3-benzoxazol-6-yl)acetamide (Radiprodil) in a pharmaceutical acceptable carrier.

2. A kit comprising
(a) a first container containing 4-hydroxy-N-(4-methoxy-7-morpholin-4-yl-1,3-benzothiazol-2-yl)-4-methylpiperidine-1-carboxamide (TOZADENANT®)
and
(b) a second container containing 2-[4-[(4-fluorophenyl)methyl]piperidin-1-yl]-2-oxo-N-(2-oxo-3H-1,3-benzoxazol-6-yl)acetamide (Radiprodil).

3. The composition according to claim 1 wherein the ratio of TOZADENANT® to Radiprodil is from 30:1 to 1:30 by weight.

4. The kit according to claim 2 wherein the ratio of TOZADENANT® to Radiprodil is from 30:1 to 1:30 by weight.

5. The composition according to claim 1 wherein the ratio of TOZADENANT® to Radiprodil is from 10:1 to 1:10 by weight.

6. The composition according to claim 1 wherein the ratio of TOZADENANT® to Radiprodil is from 3:1 to 1:3 by weight.

7. The kit according to claim 2 wherein the ratio of TOZADENANT® to Radiprodil is from 10:1 to 1:10 by weight.

8. The kit according to claim 2 wherein the ratio of TOZADENANT® to Radiprodil is from 3:1 to 1:3 by weight.

9. The composition according to claim 1 in the form of a tablet.

10. The composition according to claim 3 in the form of a tablet.

11. The composition according to claim 5 in the form of a tablet.

12. The composition according to claim 6 in the form of a tablet.

* * * * *